(12) United States Patent
Walke et al.

(10) Patent No.: US 7,374,932 B2
(45) Date of Patent: May 20, 2008

(54) HUMAN KINASES AND POLYNUCLEOTIDES ENCODING THE SAME, AND USES THEREOF

(75) Inventors: D. Wade Walke, Spring, TX (US); Erin Hilbun, Houston, TX (US); Gregory Donoho, Portage, MI (US); C. Alexander Turner, Jr., The Woodlands, TX (US); Gwenn Hansen, Spring, TX (US); Hector BeltrandelRio, The Woodlands, TX (US); Isaac Van Sligtenhorst, Spring, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 629 days.

(21) Appl. No.: 11/025,671

(22) Filed: Dec. 29, 2004

(65) Prior Publication Data

US 2007/0270506 A1    Nov. 22, 2007

Related U.S. Application Data

(60) Division of application No. 10/010,720, filed on Nov. 13, 2001, now Pat. No. 6,858,419, which is a continuation-in-part of application No. 09/854,856, filed on May 14, 2001, now Pat. No. 6,541,252.

(60) Provisional application No. 60/206,015, filed on May 19, 2000.

(51) Int. Cl.
*C12N 1/20* (2006.01)
*C12N 15/00* (2006.01)

(52) U.S. Cl. .............. 435/320.1; 435/194; 435/252.3; 536/23.2

(58) Field of Classification Search .............. 536/23.2; 435/252.3, 320.1, 194
See application file for complete search history.

(56) References Cited

U.S. PATENT DOCUMENTS

| | | | |
|---|---|---|---|
| 4,190,496 A | 2/1980 | Rubenstein et al. |
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,683,195 A | 7/1987 | Mullis et al. |
| 4,683,202 A | 7/1987 | Mullis |
| 4,689,405 A | 8/1987 | Frank et al. |
| 4,713,326 A | 12/1987 | Dattagupta et al. |
| 4,800,159 A | 1/1989 | Mullis et al. |
| 4,873,191 A | 10/1989 | Wagner et al. |
| 4,946,778 A | 8/1990 | Ladner et al. |
| 5,075,217 A | 12/1991 | Weber |
| 5,252,743 A | 10/1993 | Barrett et al. |
| 5,272,057 A | 12/1993 | Smulson et al. |
| 5,283,173 A | 2/1994 | Fields et al. |
| 5,364,759 A | 11/1994 | Caskey et al. |
| 5,424,186 A | 6/1995 | Fodor et al. |
| 5,445,934 A | 8/1995 | Fodor et al. |
| 5,459,127 A | 10/1995 | Felgner et al. |
| 5,464,764 A | 11/1995 | Capecchi et al. |
| 5,468,614 A | 11/1995 | Fields et al. |
| 5,487,992 A | 1/1996 | Capecchi et al. |
| 5,491,084 A | 2/1996 | Chalfie et al. |
| 5,556,752 A | 9/1996 | Lockhart et al. |
| 5,625,048 A | 4/1997 | Tsien et al. |
| 5,627,059 A | 5/1997 | Capecchi et al. |
| 5,631,153 A | 5/1997 | Capecchi et al. |
| 5,667,973 A | 9/1997 | Fields et al. |
| 5,700,637 A | 12/1997 | Southern |
| 5,744,305 A | 4/1998 | Fodor et al. |
| 5,777,079 A | 7/1998 | Tsien et al. |
| 5,789,215 A | 8/1998 | Berns et al. |
| 5,795,737 A | 8/1998 | Seed et al. |
| 5,804,387 A | 9/1998 | Cormack et al. |
| 5,830,721 A | 11/1998 | Stemmer et al. |
| 5,837,458 A | 11/1998 | Minshull et al. |
| 5,874,304 A | 2/1999 | Zolotukhin et al. |
| 5,877,397 A | 3/1999 | Lonberg et al. |
| 5,948,767 A | 9/1999 | Scheule et al. |
| 5,958,713 A | 9/1999 | Thastrup et al. |
| 5,968,750 A | 10/1999 | Zolotukhin et al. |
| 5,976,796 A | 11/1999 | Szalay et al. |
| 6,020,192 A | 2/2000 | Muzyczka et al. |
| 6,027,881 A | 2/2000 | Pavlakis et al. |
| 6,054,321 A | 4/2000 | Tsien et al. |
| 6,075,181 A | 6/2000 | Kucherlapati et al. |
| 6,087,555 A | 7/2000 | Dunstan et al. |
| 6,096,865 A | 8/2000 | Michaels |
| 6,110,490 A | 8/2000 | Thierry |
| 6,136,566 A | 10/2000 | Sands et al. |
| 6,139,833 A | 10/2000 | Burgess et al. |

(Continued)

OTHER PUBLICATIONS

Askew et al, 1989, "Molecular Recognition with Convergent Functional Groups, 6. Synthetic and Structural Studies with a Model Receptor for Nucleic Acid Components", J. Am. Chem. Soc. 111:1082-1090.

(Continued)

*Primary Examiner*—Maryam Monshipouri
(74) *Attorney, Agent, or Firm*—Lance K Ishimoto; Peter G Seferian

(57) ABSTRACT

Novel human polynucleotide and polypeptide sequences are disclosed that can be used in therapeutic, diagnostic, and pharmacogenomic applications.

5 Claims, No Drawings

U.S. PATENT DOCUMENTS

| | | | |
|---|---|---|---|
| 6,146,826 | A | 11/2000 | Chalfie et al. |
| 6,150,584 | A | 11/2000 | Kucherlapati et al. |
| 6,172,188 | B1 | 1/2001 | Thastrup et al. |
| 6,207,371 | B1 | 3/2001 | Zambrowicz et al. |
| 6,265,548 | B1 | 7/2001 | Pavlakis et al. |

OTHER PUBLICATIONS

Bird et al, 1988, "Single-Chain Antigen-Binding Proteins", Science 242:423-426.

Bitter et al, 1987, "Expression and Secretion Vectors for Yeast", Methods in Enzymology 153:516-544.

Brisson et al, 1984, "Expression of a bacterial gene in plants by using a viral vector", Nature 310:511-514.

Broglie et al, 1984, "Light-Regulated Expression of a Pea Ribulose-1,5-Bisphosphate Carboxylase Small Subunit Gene in Transformed Plant Cells", Science 224: 838-843.

Chien et al, 1991, "The two-hybrid system: A method to identify and clone genes for proteins that interact with a protein of interest", Proc. Natl. Acad. Sci. USA 88:9578-9582.

Colbere-Garapin et al, 1981, "A New Dominant Hybrid Selective Marker for Higher Eukaryotic Cells", J. Mol. Biol. 150:1-14.

Coruzzi et al, 1984, "Tissue-specific and light-regulated expression of a pea nuclear gene encoding the small subunit of ribulose-1,5-biphosphate carboxylase", EMBO Journal 3(8):1671-1679.

Cote et al, 1983, "Generation of human monoclonal antibodies reactive with cellular antigens", PNAS 80:2026-2030.

Gautier et al, 1987, "α-DNA IV:α-anomeric and β-anomeric tetrathymidylates covalently linked to intercalating oxazolopyridocarbazole. Synthesis, physiochemical properties and poly (rA) binding", Nucleic Acids Research 15(16):6625-6641.

Gordon, 1989, "Transgenic Animals", International Review of Cytology, 115:171-229.

Greenspan et al, 1993, "Idiotypes: structure and immunogenicity", FASEB Journal 7:437-444.

Gu et al, 1994, "Deletion of a DNA Polymerase β Gene Segment in T Cells Using Cell Type-Specific Gene Targeting", Science 265:103-106.

Gurley et al, 1986, "Upstream Sequences Required for Efficient Expression of a Soybean Heat Shock Gene", Mol. & Cell. Biology 6(2):559-565.

Houghten et al, 1991, "Generation and use of synthetic peptide combinatorial libraries for basic research and drug discovery", Nature 354:84-86.

Huse et al, 1989, "Generation of a Large Combinatorial Library of the Immunoglobulin Repertoire in Phage Lambda", Science 246:1275-1281.

Huston et al, 1988, "Protein engineering of antibody binding sites: Recovery of specific activity in an anti-digoxin single-chain Fv analogue produced in *Escherichia coli*", Proc. Natl. Acad. Sci. USA 85:5879-5883.

Inoue et al, 1987, "Sequence-dependent hydrolysis of RNA using modified oligonucleotide splints and R Nase H", FEBS Letters 215(2):327-330.

Inoue et al, 1987, "Synthesis and hybridization studies on two complementary nona(2'-O-methyl)ribonucleotides", Nucleic Acids Research 15(15):6131-6149.

Inouye & Inouye, 1985, "Up-promoter mutations in the Ipp gene of *Escherichia coli*", Nucleic Acids Research 13(9):3101-3110.

Irwin, 1968, "Comprehensive Observational Assessment: Ia. A Systematic, Quantitative Procedure for Assessing the Behavioral and Physiologic State of the Mouse", Psychopharmacologia (Berl.) 13:222-257.

Janknecht et al, 1991, "Rapid and efficient purification of native histidine-tagged protein expressed by recombinant vaccinia virus", PNAS 88:8972-8976.

Kohler & Milstein, 1975, "Continuous cultures of fused cells secreting antibody of predefined specificity", Nature 256:495-497.

Krege et al, 1995, "A Noninvasive Computerized Tail-Cuff System for Measuring Blood Pressure in Mice", Hypertension 25(5)1111-1115.

Lakso et al, 1992, "Targeted oncogene activation by site-specific recombination in transgenic mice", Proc. Natl. Acad. Sci. USA 89:6232-6236.

Lam et al, 1991, "A new type of synthetic peptide library for identifying ligand-binding activity", Nature 354:82-84.

Lavitrano et al, 1989, "Sperm Cells as Vectors for Introducing Foreign DNA into Eggs: Genetic Transformation of Mice", Cell 57:717-723.

Lewis et al, 1989, "Automated site-directed drug design: the concept of spacer skeletons for primary structure generation", Proc. R. Soc. Lond B236:125-140.

Lewis et al, 1989, "Automated site-directed drug design: the formation of molecular templates in primary structure generation", Proc. R. Soc. Lond. B 236:141-162.

Lo, 1983, "Transformation by Iontophoretic Microinjection of DNA: Multiple Integrations without Tandem Insertions", Mol. & Cell. Biology 3(10):1803-1814.

Logan et al, 1984, "Adenovirus tripartite leader sequence enhances translation of mRNAs late after infection", Proc. Natl. Acad. Sci. USA 81:3655-3659.

Lowy et al, 1980, "Isolation of Transforming DNA: Cloning the Hamster aprt Gene", Cell 22:817-823.

Luo et al, 1997, "Mammalian Two-Hybrid System: A Complementary Approach to the Yeast Two-Hybrid System", BioTechniques 22:305-352.

McKinlay et al, 1989, "Rational Design of Antiviral Agents", Annu. Rev. Pharmacol. Toxicol. 29:111-122.

Morrison and Walsh, 1988, "The Behavior and Significance of Slow-Binding Enzyme Inhibitors", Adv. Enzymol. Relat. Areas Mol. Biol. 61:201-301.

Morrison et al, 1984, "Chimeric human antibody molecules: Mouse antigen-binding domains with human constant region domains", Proc. Natl. Acad. Sci. USA 81:6851-6855.

Mulligan & Berg, 1981, "Selection for animal cells that express the *Escherichia coli* gene coding for xanthine-guanine phosphoribosyltransferase", Proc. Natl. Acad. Sci. USA 78(4):2072-2076.

Neuberger et al, 1984, "Recombinant antibodies possessing novel effector functions", Nature 312:604-608.

Nisonoff, 1991, "Idiotypes: Concepts and Applications", J. of Immunology 147:2429-2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527-1531.

Ripka, 1988, "Computers picture the perfect drug", New Scientist 16:54-57.

Ruther et al, 1983, "Easy identification of cDNA clones", EMBO Journal 2(10):1791-1794.

Santerre et al, 1984, "Expression of prokaryotic genes for hygromycin B and G418 resistance as dominant-selection markers in mouse L cells", Gene 30:147-156.

Sarin et al, 1988, "Inhibition of acquired immunodeficiency syndrome virus by oligodeoxynucleoside methylphosphonates", Proc. Natl. Acad. Sci. USA 85:7448-7451.

Smith et al, 1983, "Molecular Engineering of the *Autographa californica* Nuclear Polyhedrosis Virus Genome: Deletion Mutations within the Polyhedrin Gene", J. Virol. 46(2):584-593.

Songyang et al, 1993, "SH2 Domains Recognize Specific Phosphopeptide Sequences", Cell 72:767-778.

Stein et al, 1988, "Physiochemical properties of phosphorothioate oligodeoxynucleotides", Nucleic Acids Research 16(8):3209-3221.

Szybalska & Szybalski, 1962, "Genetics of Human Cell Lines, IV. DNA-Mediated Heritable Transformation of a Biochemical Trait", Proc. Natl. Acad. Sci. USA 48:2026-2034.

Takamatsu et al, 1987, "Expression of bacterial chloramphenicol acetyltransferase gene in tobacco plants mediated by TMV-RNA", EMBO Journal 6(2):307-311.

Takeda et al, 1985, "Construction of chimaeric processed immunoglobulin genes containing mouse variable and human constant region sequences", Nature 314:452-454.

Thompson et al, 1989, "Germ Line Transmission and Expression of a Corrected HPRT Gene Produced by Gene Targeting in Embryonic Stem Cells", Cell 56:313-321.

Van Der Putten et al, 1985, "Efficient insertion of genes into the mouse germ line via retroviral vectors", Proc. Natl. Acad. Sci. USA 82:6148-6152.

Van Heeke et al, 1989, "Expression of Human Asparagine Synthetase in *Escherichia coli*", J. Biol. Chemistry 264(10):5503-5509.

Ward et al, 1989, "Binding activities of a repertoire of single immunoglobulin variable domains secreted from *Escherichia coli*", Nature 341:544-546.

Wigler et al, 1977, "Transfer of Purified Herpes Virus Thymidine Kinase Gene to Cultured Mouse Cells", Cell 11:223-232.

Wigler et al, 1980, "Transformation of mammalian cells with an amplifiable dominant-acting gene", Proc. Natl. Acad. Sci. USA 77(6):3567-3570.

Wilson et al, 2001, "Human Hypertension Caused by Mutations in WNK Kinases", Science 293:1107-1112.

Williams and Cole, 2001, "Kinase chips hit the proteomics era", TRENDS in Biochemical Sciences 26(5):271-273.

HUMAN KINASES AND POLYNUCLEOTIDES ENCODING THE SAME, AND USES THEREOF

The present application is a divisional of U.S. application Ser. No. 10/010,720, filed Nov. 13, 2001 now U.S. Pat. No. 6,858,419, which is a continuation-in-part of U.S. application Ser. No. 09/854,856, filed on May 14, 2001, which issued as U.S. Pat. No. 6,541,252 on Apr. 1, 2003, which claims the benefit of U.S. Provisional Application No. 60/206,015, filed on May 19, 2000, each of which are herein incorporated by reference in their entirety.

The present application contains a Sequence Listing of SEQ ID NOS:1-64, submitted on one duplicate compact disc, for a total of two compact discs. The Sequence Listing with SEQ ID NOS:1-64 totals 254 pages. The Sequence Listing submitted on compact disc is herein incorporated into the specification by reference in its entirety.

1.0 FIELD OF THE INVENTION

The present invention relates to the discovery, identification, and characterization of novel human polynucleotides encoding proteins that share sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or overexpress the disclosed genes, antagonists and agonists of the proteins, and other compounds that modulate the expression or activity of the proteins encoded by the disclosed genes, which can be used for diagnosis, prognosis, drug screening, clinical trial monitoring, the treatment of diseases and disorders, such as high blood pressure, and cosmetic or nutriceutical applications.

2.0 BACKGROUND OF THE INVENTION

Kinases mediate the phosphorylation of a wide variety of proteins and compounds in the cell. Along with phosphatases, kinases are involved in a range of regulatory pathways. Given the physiological importance of kinases, they have been subject to intense scrutiny, and are proven drug targets.

Hypertension, or high blood pressure, is a major public health problem, and is defined as the condition of having blood pressure (BP) exceeding an upper limit of normality. In humans, the upper limit is generally accepted as a systolic BP of greater than 140 mg Hg and/or diastolic BP of greater than 90 mg Hg. In the majority of cases, patients are affected by essential hypertension, which by definition means that the underlying etiologic mechanism(s) causing the hypertension is unknown. Regardless of the mechanism, a sustained elevation of blood pressure for a period of time has been shown to result in significant cardiovascular damage throughout the body, e.g., congestive heart failure, coronary artery disease, stroke, kidney failure, and progressive renal failure. Hypertension is believed to affect 60 million people in the United States, and believed to account for approximately 50% of mortality beyond age 65.

It is generally accepted that a significant elevation of blood pressure can accelerate the aging process in the circulatory system. During aging, many factors involved in regulating blood pressure can go awry. Therefore it is not surprising that systolic and diastolic blood pressure increase progressively with aging, a phenomenon which is called "age-related hypertension". Hypertension is found in 50% or more of individuals above age 55 years, and 63% of those age 65 to 74 years. The rate is 76% among persons of African origin over 65 years old in the United States. This age-related hypertension, particularly of the diastolic blood pressure, is most likely due to the reduced elasticity of the blood vessels or, even worse, stiffness of the blood vessels. This reduced elasticity may be caused by damage of the muscle layer of the blood vessels. This damage can be caused by radicals from chemicals, radiation or other toxins. Due to this, these endothelial muscles cannot function properly in contracting and relaxing when blood pressure demand makes that necessary. The consequence is a higher diastolic blood pressure.

There are numerous substances in use against higher blood pressure, such as angiotensin-converting enzyme (ACE) inhibitors, beta-blockers, calcium-antagonists, diuretics, vasodilatators, and combinations thereof. However, currently available anti-hypertensive agents are not without side effects, such as the elevation of blood lipids and glucose. The elevation of blood lipids and glucose by these agents has been suggested as a reason why anti-hypertensive agents have not demonstrated any benefit to patients being monitored in death rate studies.

Therefore, there exists an outstanding need to develop new drugs to treat hypertension.

3.0 SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein, collectively referred to herein as ENZ66 (ENZ66 is also referred to as WNK1), share structural similarity with animal kinases, including, but not limited to, mitogen activated protein (MAP) kinases, serine/threonine protein kinases, P21-activated protein kinases, and NPK1-related protein kinases. As such, the novel polynucleotides encode novel kinases having homologues and orthologs across a range of phyla and species.

The novel human polynucleotides described herein encode open reading frames (ORFs) encoding proteins of 2382, 2245, 982, 2229, 2092, 829, 2136, 1999, 2354, 2217, 954, 2201, 2064, 801, 2108, 1971, 2322, 2185, 922, 2169, 2032, 769, 2076, 1939, 2294, 2157, 894, 2141, 2004, 741, 2048, and 1911 amino acids in length (see respectively SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58 60, 62, and 64). The present invention also provides vectors, including, but not limited to, expression vectors, that include or express unique ENZ66 nucleotide and/or protein, polypeptide or peptide sequences. Additionally, the unique ENZ66 sequences described in SEQ ID NOS:1-64 are useful for the identification of coding sequences and the mapping of a unique gene to a particular chromosome.

The present invention also includes host cells, such as murine ES cells, that comprise one or more of the present ENZ66 sequences, and both transgenic animals that express an ENZ66 transgene, and ENZ66 "knock-outs" (which can be conditional) that do not express a functional ENZ66. To this end, several gene trapped knockout ES cells have been generated in murine homologs of ENZ66. Homozygous mutants, in which both copies of the ENZ66 gene have been disrupted, die prior to birth. Therefore ENZ66 appears to play a critical role in metabolism and/or development. Characterization of mice in which one copy of ENZ66 has been disrupted (heterozygotes) has allowed the identification of a novel role for this enzyme, and a model for the study of certain metabolic disorders. In particular, ENZ66 knockout mice (that are heterozygous for the mutated gene) display, intra alia, decreased blood pressure levels. This suggests that these mice can be used as models for the study of a variety of human conditions, including, but not limited to, hypertension (including essential and age-related hypertension), and conditions associated with hypertension, including, but not limited to, congestive heart failure, coronary artery disease, stroke, kidney failure, and progressive renal failure.

In addition, the invention includes animals containing at least a single disrupted ENZ66 allele (e.g., "knock-out" mice) that do not express normal levels of ENZ66, such as those described in the examples below, humanized "knock-in" animals where the endogenous murine ENZ66 gene has been replaced by one or more polynucleotides encoding at least a first human ENZ66 protein, or animals harboring one or more ENZ66 transgene (e.g., mice overexpressing ENZ66). These animals may either transiently, inducibly, or constitutively express ENZ66.

Further, the present invention also relates to processes for identifying compounds that modulate, i.e., act as agonists or antagonists, of ENZ66 expression and/or ENZ66 protein activity, that utilize purified preparations of the described ENZ66 polynucleotides and/or ENZ66 proteins, polypeptides or peptides, or cells expressing the same. The agonists and antagonists of ENZ66 include small molecules, large molecules, mutant versions of ENZ66, or portions thereof, that compete with native ENZ66, ENZ66 peptides, and antibodies, as well as nucleotide sequences that can be used to inhibit the expression of ENZ66 (e.g., antisense and ribozyme molecules, and gene or regulatory sequence replacement constructs) or to enhance the expression of ENZ66 polynucleotides (e.g., expression constructs that place ENZ66 under the control of a strong promoter system). Such compounds can be used as prophylactic or therapeutic agents for the prevention or treatment of any of a wide variety of symptoms associated with certain biological disorders or imbalances, such as hypertension.

The present invention also provides novel methods and compositions that can be used to facilitate drug discovery, drug development, and/or as treatments of conditions such as high blood pressure, and the complications resulting therefrom. The present invention is based on the identification and novel functional characterization of ENZ66, as described herein.

The invention encompasses diagnostic assays that make use of the ENZ66 polynucleotide sequences, or portions thereof, host cells expressing such nucleotides, and the expression products of such nucleotides, nucleotides that encode mammalian versions of ENZ66, including human ENZ66, nucleotides that encode ENZ66 mutants and the corresponding mutant ENZ66 expression products, nucleotides that encode portions of ENZ66 that correspond to one or more of the ENZ66 functional domains and the polypeptide products specified by such nucleotide sequences, and nucleotides that encode fusion proteins containing ENZ66 or one or more of its domains fused to another polypeptide.

The present invention also features assays for the identification of compounds that modulate ENZ66 activity in the body. Such compounds can be used as agents to affect ENZ66-mediated metabolic processes, for example, as therapeutic agents for the treatment of hypertension. The present invention also contemplates methods of using mammalian ENZ66 protein(s), and particularly recombinantly expressed human ENZ66 protein(s), in cell-free and/or cell-based assays for identifying compounds (modulators) that bind to and/or antagonize or otherwise modulate (i.e., increase or decrease) ENZ66 activity. Compounds developed using such assays are then typically used in in vivo assays to determine the effect of such compounds on ENZ66-mediated metabolic processes, and to discern or verify the observed phenotypic effects. Such phenotypic effects include, but are not limited to, lowered blood pressure and/or a delay in the onset or reduction of one or more of the complications associated with hypertension. The invention thus additionally contemplates compounds that bind to and/or activate or inhibit the activity of ENZ66, as well as pharmaceutical compositions comprising such compounds, and the use of such compounds to treat ENZ66-related disorders.

In addition to small molecule agonists and antagonists of ENZ66, the invention also contemplates the use of large molecules to effect the levels or bioavailability of ENZ66 in vivo, including, but not limited to, mutant ENZ66 proteins that compete with native ENZ66, anti-ENZ66 antibodies, anti-idiotypic antibodies that bind anti-ENZ66 antibodies or ENZ66 binding partners, nucleotide sequences that can be used to inhibit ENZ66 expression (e.g., antisense, ribozyme and/or triplex molecules, and coding sequence or regulatory sequence replacement constructs) or to enhance ENZ66 expression (e.g., expression constructs that place an ENZ66 sequence under the control of a strong promoter or expression system).

In addition, the invention encompasses methods and compositions for the diagnostic evaluation, typing and prognosis of ENZ66-mediated disorders, including, inter alia, hypertension and related conditions, such as congestive heart failure, coronary artery disease, stroke, kidney failure, and progressive renal failure, and for the identification of subjects having a predisposition to such conditions.

For example, in another embodiment of the present invention, ENZ66 nucleic acid molecules of the invention can be used as diagnostic hybridization probes or as primers for diagnostic PCR analysis for the identification of ENZ66 gene mutations, allelic variations, and/or regulatory defects in an ENZ66 gene. ENZ66 sequences may be used in hybridization or amplification assays of biological samples to detect abnormalities involving ENZ66 gene structure, including point mutations, insertions, deletions and/or chromosomal rearrangements. Such diagnostic assays include, but are not limited to, Southern analyses, single stranded conformational polymorphism analyses (SSCP), restriction fragment length polymorphisms (RFLP), coding single nucleotide polymorphisms (cSNP) and PCR analyses. These assays can be combined with "gene chip" technology and used to screen pre-existing genetic databases of patients suffering from various ENZ66-mediated disorders. The sequences of the present invention are also useful as additional DNA markers for forensic biology. The present invention further provides for diagnostic kits for practicing such methods.

4.0 DESCRIPTION OF THE SEQUENCE LISTING AND FIGURES

The Sequence Listing provides the sequences of the novel human ORFs encoding the described novel human ENZ66 kinase proteins, as well as the amino acid sequences of the encoded novel human ENZ66 kinase proteins. As used herein, ENZ66 will be understood to refer to one or more of the sequences (SEQ ID NOS:1-64) presented in the Sequence Listing.

5.0 DETAILED DESCRIPTION OF THE INVENTION

ENZ66, described for the first time herein, are novel proteins that are expressed in, inter alia, human cell lines, and human fetal brain, brain, pituitary, cerebellum, spinal cord, thymus, spleen, lymph node, bone marrow, trachea, lung, kidney, fetal liver, liver, prostate, testis, thyroid, adrenal gland, pancreas, salivary gland, stomach, small intestine, colon, skeletal muscle, heart, uterus, placenta, mammary gland, adipose, skin, esophagus, bladder, cervix, rectum, pericardium, eye, ovary, fetal kidney, fetal lung, gall bladder, tongue, aorta, embryo (6, 9 and 12 weeks), adenocarcinoma (adrenal cortex), osteosarcoma, embryonic carcinoma, umbilical vein, microvascular endothelium and gene trapped cells. The described sequences were compiled from gene trapped sequences in conjunction with sequences available in GENBANK, and cDNAs were isolated from a brain library (Edge Biosystems, Gaithersburg, Md.).

Hypertension, or high blood pressure, is a major public health problem, and is defined as the condition of having blood pressure exceeding the normal upper limit. As discussed above, current treatments for high blood pressure suffer from a number of drawbacks, thus highlighting the need for new treatments for hypertension. The present disclosure details that mice in which even one allele of the murine homolog of human ENZ66 has been disrupted have markedly lower blood pressure that wild-type litter mates. Therefore, antagonists of ENZ66 appear to be ideal candidates for use in the treatment of hypertension. A link between this serine-threonine kinase (WNK1) and hypertension in humans has recently been suggested (Wilson et al., 2001, Science 293:1107-1112).

The present invention encompasses the nucleotides presented in the Sequence Listing, host cells expressing such nucleotides, the expression products of such nucleotides, and: (a) nucleotides that encode mammalian homologs of ENZ66, including the specifically described ENZ66 sequences, and the ENZ66 amino acid products; (b) nucleotides that encode one or more portions of ENZ66 that correspond to functional domains, and the polypeptide products specified by such nucleotide sequences, including, but not limited to, the novel regions of any active domain(s); (c) isolated nucleotides that encode mutant versions, engineered or naturally occurring, of ENZ66 in which all or a part of at least one domain is deleted or altered, and the polypeptide products specified by such nucleotide sequences, including, but not limited to, soluble proteins and peptides in which all or a portion of the signal sequence is deleted; (d) nucleotides that encode chimeric fusion proteins containing all or a portion of a coding region of ENZ66, or one of its domains (e.g., a receptor/ligand binding domain, accessory protein/self-association domain, etc.) fused to another peptide or polypeptide; and (e) therapeutic or diagnostic derivatives of the described ENZ66 polynucleotides, Including, but not limited to, oligonucleotides, antisense polynucleotides, ribozymes, dsRNA, or gene therapy constructs comprising a sequence first disclosed in the Sequence Listing.

The present invention also includes murine ENZ66, mutated murine embryonic stem cell clones, and animals derived from these embryonic stem cells. Characterization of mice in which ENZ66 gene function has been disrupted (knock-outs) indicates that ENZ66 plays a role in conditions including, but not limited to, hypertension, one or more of the complications arising from hypertension, and other disorders, as detailed herein.

The invention encompasses the use of ENZ66 nucleotides, ENZ66 proteins and peptides, as well as antibodies to ENZ66 (that can, for example, act as ENZ66 agonists or antagonists), antagonists (peptides, small organic molecules, fusion proteins, etc.) that inhibit ENZ66 activity or expression, or agonists that activate ENZ66 activity or increase its expression, in the identification, diagnosis, prognosis, and/or treatment of ENZ66-mediated disorders. The diagnosis of an ENZ66 abnormality in a patient, or an abnormality in the ENZ66 regulatory pathway, can also facilitate the development of treatments or therapeutic regimens. In addition, ENZ66 nucleotides and ENZ66 proteins can be used to identify compounds effective in the treatment of, among other things, ENZ66-mediated disorders, including, but not limited to, hypertension and related conditions, such as congestive heart failure, coronary artery disease, stroke, kidney failure, and progressive renal failure.

In addition, the present invention encompasses methods and compositions for the diagnostic evaluation, typing and prognosis of ENZ66-mediated disorders including, but not limited to, hypertension and related conditions, such as congestive heart failure, coronary artery disease, stroke, kidney failure, and progressive renal failure.

An additional embodiment of the present invention relates to methods of using ENZ66 polynucleotides and/or ENZ66 gene products (proteins, polypeptides and/or peptides) for the identification of compounds that modulate, i.e., act as agonists or antagonists, of ENZ66 gene expression and/or ENZ66 gene product activity. Such compounds can be used as agents to manipulate ENZ66-mediated disorders and, in particular, as therapeutic agents for the treatment of ENZ66-mediated disorders. Such methods and compositions are typically capable of modulating the level of ENZ66 gene expression and/or the level of ENZ66 gene product activity. The basis for these aspects of the present invention is the novel discovery that the elimination of a single ENZ66 allele results in, among other effects, decreased blood pressure, as shown herein below.

The invention described in the subsections below thus encompasses ENZ66 polypeptides or peptides corresponding to one or more of the functional domains of ENZ66, mutated, truncated or deleted ENZ66, ENZ66 fusion proteins (e.g., ENZ66 or one or more functional domains of ENZ66 fused to an unrelated protein or peptide, such as albumin or an immunoglobulin constant region, i.e., IgFc), nucleotide sequences encoding such products, and host cell expression systems that can produce such ENZ66 products.

The invention also encompasses antibodies and anti-idiotypic antibodies, or fragments thereof (including Fab and F(ab')$_2$ fragments), antagonists and agonists of ENZ66, as well as compounds or nucleotide constructs that inhibit expression of the ENZ66 gene (transcription factor inhibitors, antisense and ribozyme molecules, and/or coding sequence or regulatory sequence replacement constructs), or promote expression or overexpression of ENZ66 (e.g., expression constructs in which ENZ66 coding sequences are operatively associated with expression control elements, such as promoters, promoter/enhancers, etc.).

The ENZ66 proteins, polypeptides or peptides, ENZ66 fusion proteins, ENZ66 nucleotide sequences, antibodies, antagonists and/or agonists can be useful for the detection of mutant ENZ66 or inappropriately expressed ENZ66, which can be used, for example, to diagnose ENZ66-mediated disorders. The ENZ66 proteins or peptides, ENZ66 fusion proteins, ENZ66 nucleotide sequences, host cell expression systems, antibodies, antagonists, agonists and genetically engineered cells and animals can also be used for screening for drugs (or high throughput screening of combinatorial libraries) effective in the treatment of the symptomatic or phenotypic manifestations of perturbing the normal function of ENZ66 in the body. The use of engineered host cells and/or animals can offer an advantage in that such systems allow not only for the identification of compounds that bind to the endogenous receptor/ligand of ENZ66, but can also identify compounds that trigger ENZ66-mediated activities or pathways.

Where, as in the present instance, some of the described ENZ66 peptides or polypeptides are thought to be cytoplasmic or nuclear proteins (although processed forms or fragments can be secreted or membrane associated), expression systems can be engineered that produce soluble derivatives of ENZ66 (such as those corresponding to ENZ66 extracellular and/or intracellular domains, or truncated ENZ66 polypeptides lacking one or more hydrophobic domains) and/or ENZ66 fusion protein products (especially ENZ66-Ig fusion proteins, i.e., fusions of one or more ENZ66 domain(s) to an IgFc). These expression products, as well as ENZ66 antibodies, anti-idiotypic antibodies (including Fab fragments), and ENZ66 antagonists or agonists (including compounds that modulate or act on downstream targets in an ENZ66-mediated pathway), can be used to directly treat diseases or disorders. For instance, the administration of an effective amount of soluble ENZ66, or an ENZ66-IgFc fusion protein or an anti-idiotypic antibody (or its Fab) that mimics ENZ66 could activate or effectively antagonize the endogenous ENZ66 or a protein interactive therewith. Nucleotide constructs encoding such ENZ66 products can be used to genetically engineer host cells to express such products in vivo; these genetically engineered cells function as "bioreactors" in the body, delivering a continuous supply of ENZ66, an ENZ66 peptide, or an ENZ66 fusion protein to the body. Nucleotide constructs encoding functional ENZ66, mutant ENZ66, as well as antisense and ribozyme molecules, can also be used in "gene therapy" approaches for the modulation of ENZ66 expression (and, consequently, modulating blood pressure higher or lower). Thus, the invention also encompasses pharmaceutical formulations and methods for treating biological disorders.

Various aspects of the invention are described in greater detail in the subsections below.

5.1 the ENZ66 Nucleotide Sequences

The cDNA sequences and corresponding deduced amino acid sequences of ENZ66 are presented in the Sequence Listing.

Expression analysis has provided evidence that ENZ66 can be expressed in a wide range of human tissues, as described herein, as well as gene trapped human cells. In addition to serine/threonine kinases, ENZ66 also shares significant similarity to a range of additional kinase families from a variety of phyla and species.

A number of polymorphisms can occur in ENZ66, such as a possible A-T transversion that can occur in the sequence region corresponding to, for example, nucleotide position 2929 of SEQ ID NOS:1, 3 and 5, which can result in a serine or threonine being present in the corresponding amino acid sequence represented by, for example, position 977 of SEQ ID NOS:2, 4 and 6; a possible G-T transversion at the sequence position represented by, for example, nucleotide 5424 of SED ID NOS:1 and 3, which can result in a methionine or isoleucine being present in the corresponding amino acid sequence represented by, for example, position 1808 of SEQ ID NOS:2 and 4; a possible A-T transversion that can occur in the sequence region corresponding to, for example, nucleotide position 2470 of SEQ ID NOS:7, 9 and 11, which can result in a serine or threonine being present in the corresponding amino acid sequence represented by, for example, position 824 of SEQ ID NOS:8, 10 and 12; a possible G-T transversion at the sequence position represented by, for example, nucleotide 4965 of SED ID NOS:7 and 9, which can result in a methionine or isoleucine being present in the corresponding amino acid sequence represented by, for example, position 1655 of SEQ ID NOS:8 and 10; a possible G-T transversion at the sequence position represented by, for example, nucleotide 4686 of SED ID NOS:13 and 15, which can result in a methionine or isoleucine being present in the corresponding amino acid sequence represented by, for example, position 1562 of SEQ ID NOS:14 and 16; a possible A-T transversion that can occur in the sequence region corresponding to, for example, nucleotide position 2845 of SEQ ID NOS:17, 19 and 21, which can result in a serine or threonine being present in the corresponding amino acid sequence represented by, for example, position 949 of SEQ ID NOS:18, 20 and 22; a possible G-T transversion at the sequence position represented by, for example, nucleotide 5340 of SED ID NOS:17 and 19, which can result in a methionine or isoleucine being present in the corresponding amino acid sequence represented by, for example, position 1780 of SEQ ID NOS:18 and 20; a possible A-T transversion that can occur in the sequence region corresponding to, for example, nucleotide position 2386 of SEQ ID NOS:23, 25 and 27, which can result in a serine or threonine being present in the corresponding amino acid sequence represented by, for example, position 796 of SEQ ID NOS:24, 26 and 28; a possible G-T transversion at the sequence position represented by, for example, nucleotide 4881 of SED ID NOS:23 and 25, which can result in a methionine or isoleucine being present in the corresponding amino acid sequence represented by, for example, position 1627 of SEQ ID NOS:24 and 26; a possible G-T transversion at the sequence position represented by, for example, nucleotide 4602 of SED ID NOS:29 and 31, which can result in a methionine or isoleucine being present in the corresponding amino acid sequence represented by, for example, position 1534 of SEQ ID NOS:30 and 32; a possible A-T transversion that can occur in the sequence region corresponding to, for example, nucleotide position 2749 of SEQ ID NOS:33, 35 and 37, which can result in a serine or threonine being present in the corresponding amino acid sequence represented by, for example, position 917 of SEQ ID NOS:34, 36 and 38; a possible G-T transversion at the sequence position represented by, for example, nucleotide 5244 of SED ID NOS:33 and 35, which can result in a methionine or isoleucine being present in the corresponding amino acid sequence represented by, for example, position 1748 of SEQ ID NOS:34 and 36; a possible A-T transversion that can occur in the sequence region corresponding to, for example, nucleotide position 2290 of SEQ ID NOS:39, 41 and 43, which can result in a serine or threonine being present in the corresponding amino acid sequence represented by, for example, position 764 of SEQ ID NOS:40, 42 and 44; a possible G-T transversion at the sequence position represented by, for example, nucleotide 4785 of SED ID NOS:39 and 41, which can result in a methionine or isoleucine being present in the corresponding amino acid sequence represented by, for example, position 1595 of SEQ ID NOS:40 and 42; a possible G-T transversion at the sequence position represented by, for example, nucleotide 4506 of SED ID NOS:45 and 47, which can result in a methionine or isoleucine being present in the corresponding amino acid sequence represented by, for example, position 1502 of SEQ ID NOS:46 and 48; a possible A-T transversion that can occur in the sequence region corresponding to, for example, nucleotide position 2665 of SEQ ID NOS:49, 51 and 53, which can result in a serine or threonine being present in the corresponding amino acid sequence represented by, for example, position 889 of SEQ ID NOS:50, 52 and 54; a possible G-T transversion at the sequence position represented by, for example, nucleotide 5160 of SED ID NOS:49 and 51, which can result in a methionine or isoleucine being present in the corresponding amino acid sequence represented by, for example, position 1720 of SEQ ID NOS:50 and 52; a possible A-T transversion that can occur in the sequence region corresponding to, for example, nucleotide position 2206 of SEQ ID NOS:55, 57 and 59, which can result in a serine or threonine being present in the corresponding amino acid sequence represented by, for example, position 736 of SEQ ID NOS:56, 58 and 60; a possible G-T transversion at the sequence position represented by, for example, nucleotide 4701 of SEQ ID NOS:55 and 57, which can result in a methionine or isoleucine being present in the corresponding amino acid sequence represented by, for example, position 1567 of SEQ ID NOS:56 and 58; and a possible G-T transversion at the sequence position represented by, for example, nucleotide 4422 of SED ID NOS:61 and 63, which can result in a methionine or isoleucine being present in the corresponding amino acid sequence represented by, for example, position 1474 of SEQ ID NOS:62 and 64.

As discussed above, the present invention includes the human DNA sequences presented in the Sequence Listing (and vectors comprising the same), and additionally contemplates any nucleotide sequence encoding a contiguous ENZ66 open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., New York, at p. 2.10.3), and encodes a functionally equivalent ENZ66 gene product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent ENZ66 product. Functional equivalents of ENZ66 include, but are not limited to, naturally occurring versions of ENZ66 present in other species, and mutant versions of ENZ66, whether naturally occurring or engineered (by site directed mutagenesis, gene shuffling, or directed evolution, as described in, for example, U.S. Pat. No. 5,837,458, which is incorporated herein by reference in its entirety). The invention also includes degenerate nucleic acid variants of the disclosed ENZ66 polynucleotide sequences.

Additionally contemplated are polynucleotides encoding ENZ66 ORFs, or their functional equivalents, encoded by polynucleotide sequences that are about 99, 95, 90, or about 85 percent similar to corresponding regions of SEQ ID NO:1 (as measured by BLAST sequence comparison analysis using, for example, the University of Wisconsin GCG sequence analysis package (SEQUENCHER 3.0, Gene Codes Corp., Ann Arbor, Mich.) using default parameters).

The invention also includes nucleic acid molecules, preferably DNA molecules, that hybridize to, and are therefore the complements of, the described ENZ66-encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc. Alternatively, such ENZ66 oligonucleotides can be used as hybridization probes for screening libraries, and assessing gene expression patterns (particularly using a microarray or high-throughput "chip" format), as described in greater detail below.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific ENZ66 oligonucleotide sequence(s) first disclosed in SEQ ID NOS:1-64. Alternatively, a restriction map specifying the relative positions of restriction endonuclease digestion sites, or various palindromic or other specific oligonucleotide sequences, can be used to structurally describe a given sequence. Such restriction maps, which are typically generated by widely available computer programs (e.g., the University of Wisconsin GCG sequence analysis package, etc.), can optionally be used in conjunction with one or more discrete nucleotide sequence(s) present in the sequence that can be described by the relative position of the sequence relative to one or more additional sequence(s), or one or more restriction sites, present in the disclosed sequence.

These nucleic acid molecules may encode or act as ENZ66 gene antisense molecules, useful, for example, in ENZ66 gene regulation and/or as antisense primers in amplification reactions of ENZ66 nucleic acid sequences. With respect to ENZ66 gene regulation, such techniques can be used to regulate one or more of the biological functions associated with ENZ66, as described herein. Further, such sequences can be used as part of ribozyme and/or triple helix sequences that are also useful for ENZ66 gene regulation.

Inhibitory antisense or double stranded oligonucleotides can additionally comprise at least one modified base moiety that is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotides can also comprise at least one modified sugar moiety selected from the group including, but not limited to, arabinose, 2-fluoroarabinose, xylulose, and hexose.

In yet another embodiment, the antisense oligonucleotides will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotides are α-anomeric oligonucleotides. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641). The oligonucleotide can also be a 2'-0-methylribonucleotide (Inoue et al., 1987, Nucl. Acids Res. 15:6131-6148), or a chimeric RNA-DNA analogue (Inoue et al., 1987, FEBS Lett. 215:327-330). Alternatively, double stranded RNA can be used to disrupt the expression and function of ENZ66.

Further, ENZ66 homologs and orthologs can be isolated from nucleic acids from additional mammalian species, for example, by performing PCR using two degenerate or "wobble" oligonucleotide primer pools designed on the basis of amino acid sequences within the ENZ66 sequences disclosed herein. The template for the reaction may be total RNA, mRNA, and/or cDNA obtained by reverse transcription of mRNA prepared from, for example, human or non-human cell lines, cell types, or tissues known to express, or suspected of expressing, an allele of an ENZ66 gene.

The PCR product can be sequenced directly, or subcloned and sequenced, to ensure that the amplified sequences represent ENZ66 coding sequences. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known to express, or suspected of expressing, ENZ66). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

ENZ66 sequences can also be used to isolate mutant alleles of ENZ66. Such mutant alleles can be isolated from individuals either known to have, or suspected of having, a genotype that contributes to hypertension, or other symptoms or complications related to hypertension, as described herein. Mutant alleles and/or peptides, polypeptides or proteins may then be utilized in the therapeutic and diagnostic programs described herein. Additionally, such sequences of any of the genes corresponding to ENZ66 can be used to detect gene regulatory (e.g., promoter or promoter/enhancer) defects that can affect, for example, blood pressure.

A cDNA encoding a mutant ENZ66 gene or sequence can be isolated, for example, by using PCR. In this case, the first cDNA strand may be synthesized by hybridizing an oligo-dT oligonucleotide to mRNA isolated from tissue known to express or suspected of expressing a mutant ENZ66 gene in an individual putatively carrying a mutant ENZ66 allele, and by extending the new strand with reverse transcriptase. The second strand of the cDNA is then synthesized using an oligonucleotide that hybridizes specifically to the 5' end of the normal ENZ66 gene. Using these two primers, the product is then amplified via PCR, optionally cloned into a suitable vector, and subjected to DNA sequence analysis through methods well known to those of skill in the art. By comparing the DNA sequence of the mutant ENZ66 allele to that of a corresponding normal ENZ66 allele, the mutation(s) responsible for the loss or alteration of function of the mutant ENZ66 gene product can be ascertained.

Alternatively, a genomic library can be constructed using DNA obtained from an individual suspected of carrying, or known to carry, a mutant ENZ66 allele (e.g., a person manifesting a ENZ66-associated phenotype such as, for example, high blood pressure, or complications associated with high blood pressure), or a cDNA library can be constructed using RNA from a tissue known to express, or suspected of expressing, a mutant ENZ66 allele. A normal ENZ66 gene, or any suitable fragment thereof, can then be labeled and used as a probe to identify the corresponding mutant ENZ66 allele in such libraries. Clones containing mutant ENZ66 gene sequences can then be purified and subjected to sequence analysis according to methods well known to those skilled in the art.

Additionally, an expression library can be constructed utilizing cDNA synthesized from, for example, RNA isolated from a tissue known to express, or suspected of expressing, a mutant ENZ66 allele in an individual suspected of carrying, or known to carry, such a mutant allele. In this manner, gene products made by the putatively mutant tissue may be expressed and screened using standard antibody screening techniques in conjunction with antibodies raised against a normal ENZ66 product, as described below (for screening techniques, see, for example, Harlow and Lane, eds., 1988, "Antibodies: A Laboratory Manual", Cold Spring Harbor Press, Cold Spring Harbor, N.Y., incorporated herein by reference in its entirety).

Additionally, screening can be accomplished by screening with labeled ENZ66 fusion proteins, such as, for example, alkaline phosphatase-ENZ66 or ENZ66-alkaline phosphatase fusion proteins. In cases where an ENZ66 mutation results in an expressed gene product with altered function (e.g., as a result of a missense or a frameshift mutation), polyclonal antibodies to ENZ66 are likely to cross-react with a corresponding mutant ENZ66 gene product. Library clones detected via their reaction with such labeled antibodies can be purified and subjected to sequence analysis according to methods well known in the art.

The invention also encompasses nucleotide sequences that encode mutant isoforms of any of the ENZ66 amino acid sequences, peptide fragments thereof, truncated versions thereof, and/or fusion proteins, including any of the above fused to another unrelated polypeptide. Examples of such polypeptides can include, but are not limited to, an epitope tag that aids in purification or detection of the resulting fusion protein, or an enzyme, fluorescent protein, or luminescent protein that can be used as a marker.

The present invention additionally encompasses: (a) RNA or DNA vectors that contain any portion of ENZ66 and/or their complements, as well as any of the peptides or proteins encoded thereby; (b) DNA vectors that contain a cDNA that substantially spans the entire open reading frame corresponding to any of the sequences of ENZ66 and/or their complements; (c) DNA expression vectors that contain any of the foregoing sequences, or a portion thereof, operatively associated with a regulatory element that directs the expression of the coding sequences in the host cell; and (d) genetically engineered host cells that contain a cDNA that spans the entire open reading frame, or any portion thereof, corresponding to any of the sequences of ENZ66, operatively associated with a regulatory element, which may be exogenously controlled (such as in gene activation), either in vivo and/or in vitro, which directs the expression of ENZ66 coding sequences in the host cell.

As used herein, regulatory elements include, but are not limited to, inducible and non-inducible promoters, enhancers, operators, and other elements known to those skilled in the art that drive and regulate expression. Such regulatory elements include, but are not limited to, the baculovirus polyhedrin promoter, the cytomegalovirus (hCMV) immediate early gene promoter, regulatable, viral elements (particularly retroviral LTR promoters), the early or late promoters of SV40 and adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses nucleotide constructs encoding ENZ66 products that can be used to genetically engineer host cells to express such ENZ66 products in vivo. These genetically engineered cells function as "bioreactors" in the body, delivering a continuous supply of ENZ66, ENZ66 peptides or polypeptides, soluble ENZ66, or ENZ66 fusion proteins. Nucleotide constructs encoding functional versions of ENZ66, mutant versions of ENZ66, as well as antisense and ribozyme molecules, can be used in "gene therapy" approaches for the modulation of ENZ66 expression and/or activity in the treatment of ENZ66-mediated disorders. Thus, the invention also encompasses pharmaceutical formulations and methods for treating ENZ66-mediated disorders such as hypertension, diseases related to or arising from hypertension, complications associated with hypertension, and other body composition disorders.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458, which are herein incorporated by reference in their entirety.

5.1.1 Cells that Contain ENZ66 Disrupted Alleles

Another aspect of the current invention includes cells that contain a disrupted ENZ66 gene. There are a variety of techniques that can be used to disrupt genes in cells, and especially ES cells. Examples of such methods are described in co-pending U.S. patent application Ser. No. 08/728,963, and U.S. Pat. Nos. 5,789,215, 5,487,992, 5,627,059, 5,631,153, 6,087,555, 6,136,566, 6,139,833, and 6,207,371, all of which are herein incorporated by reference in their entirety.

5.1.2 Identification of Cells that Express ENZ66

Host cells that contain ENZ66 coding sequence and/or express a biologically active ENZ66 gene product, or fragment thereof, can be identified by at least four general approaches: (a) DNA-DNA or DNA-RNA hybridization; (b) the presence or absence of "marker" gene functions; (c) assessing the level of ENZ66 transcription as measured by the expression of ENZ66 mRNA transcripts in the host cell; and (d) detection of ENZ66 gene product as measured by immunoassay, enzymatic assay, chemical assay, or one or more of the biological activities of ENZ66. These identification methods are described in greater detail below. Prior to screening for gene expression, the host cells can first be treated in an effort to increase the level of expression of sequences encoding ENZ66 polynucleotides, especially in cell lines that produce low amounts of ENZ66 mRNAs and/or ENZ66 peptides and proteins.

In approach (a) above, the presence of an ENZ66 coding sequence can be detected by DNA-DNA or DNA-RNA hybridization using probes comprising nucleotide sequences that are homologous or complementary to the ENZ66 coding sequences, as described herein, or portions or derivatives thereof.

In approach (b), the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if an ENZ66 polynucleotide sequence that encodes an ENZ66 peptide or protein is inserted within a marker gene sequence of a vector, recombinants containing an ENZ66 coding sequence can be identified by the absence of marker gene function. Alternatively, a marker gene can be placed in tandem with an ENZ66 sequence, under the control of the same or a different promoter used to control the expression of the ENZ66 coding sequence. Expression of the marker gene product in response to induction or selection indicates the presence of the ENZ66 coding sequence.

In approach (c), transcriptional activity of a coding region of ENZ66 can be assessed by hybridization assays. For example, RNA can be isolated and analyzed by Northern blot using a probe derived from ENZ66, or any portion thereof. Alternatively, total nucleic acids of the host cell may be extracted and assayed for hybridization to such probes. Additionally, RT-PCR (using ENZ66 specific oligos) may be used to detect low levels of gene expression in a sample, or in RNA isolated from a spectrum of different tissues, or in cDNA libraries derived from different tissues, to determine which tissues express a given ENZ66.

In approach (d), the expression of the peptides and proteins of the current invention can be assessed immunologically, for example by Western blots, immunoassays such as radioimmuno-precipitation, radioimmunoassays, enzyme-linked immunosorbent assays, and the like. This can be achieved by using an antibody, or a binding partner, specific to an ENZ66 peptide or protein. Additionally, expression can be assessed by monitoring one or more of the biological activities of ENZ66. ENZ66 has, among others activities, activity as a kinase, and is therefore involved in phosphorylation. Thus assays described herein, as well as those commonly known to those of skill in the art to examine kinases and phosphorylation (such as those described in "Protein Phosphorylation: A Practical Approach, Hardie, G., ed., Oxford University Press, New York), can be used to access ENZ66 biological activity.

5.1.3 the Use of ENZ66 Polynucleotide Sequences to Diagnose ENZ66-Mediated Disorders The ENZ66 polynucleotide sequences, as described above, can be used in hybridization based assays to identify and diagnose ENZ66-mediated disorders that result from mutant ENZ66 sequences, or to quantify levels of ENZ66 expression, thus identifying individuals that are at risk for developing ENZ66-mediated disorders, such as those involving hypertension. These assays could be in the form of fluorescence or enzyme based in situ hybridization, PCR, or in a preferred embodiment, hybridization probes used to assess gene expression patterns using a microarray or high-throughput "chip" format.

The present invention includes assays that utilize, among others, ENZ66 sequences (and vectors comprising the same), a open reading frame (ORF) encoding a naturally occurring protein having ENZ66 activity and that hybridizes to a complement of an ENZ66 DNA sequence under highly stringent conditions, as described herein, and encodes a functionally equivalent gene product, as described herein. The present assays also contemplate the use of any nucleotide sequences that hybridize to the complement of a nucleotide sequence that encodes ENZ66 under moderately stringent conditions, as described herein, yet still encodes a functionally equivalent ENZ66 product, as described herein.

Additionally contemplated are the use of polynucleotides encoding ENZ66 ORFs, or their functional equivalents, encoded by polynucleotide sequences that are about 99, 95, 90, or about 85 percent similar or identical to the ENZ66 nucleotide sequences (as measured by BLAST sequence comparison analysis using, for example, the University of Wisconsin GCG sequence analysis package using standard default settings).

The invention also includes the use of nucleic acid molecules preferably DNA molecules, that hybridize to, and are therefore the complements of, the described ENZ66 nucleotide sequences. Such hybridization conditions may be highly stringent or less highly stringent, as described herein. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of ENZ66 sequence. Such oligonucleotides can be used, for example, in conjunction with the polymerase chain reaction (PCR) to screen libraries, isolate clones, and prepare cloning and sequencing templates, etc.

For oligonucleotide probes, highly stringent conditions can typically refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized (Stein et al., 1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448-7451), etc.

Low stringency conditions are well-known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Cold Spring Harbor Press, NY; and Ausubel, et al., 1989, supra (and periodic updates thereof).

Alternatively, ENZ66 oligonucleotides and/or amino acids can be used as hybridization probes for screening libraries, or assessing gene expression patterns (particularly using a microarray or high-throughput "chip" format). Such assays would be applicable to the screening of large databases containing, for example, sequences obtained from patients suspected of having a ENZ66 defect. This methodology would therefore link functional information with large amounts of genetic information.

Additionally, a series of the described oligonucleotide sequences, or the complements thereof, can be used to represent all or a portion of ENZ66 sequences. An oligonucleotide, polynucleotide or amino acid sequence of ENZ66 can also be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence of ENZ66 or the amino acid sequence encoded thereby. Methods for attaching biopolymers to, or synthesizing biopolymers on, solid support matrices, and conducting binding studies thereon, are disclosed in, inter alia, U.S. Pat. Nos. 5,700,637, 5,556,752, 5,744,305, 4,631,211, 5,445,934, 5,252,743, 4,713,326, 5,424,186, and 4,689,405, the disclosures of which are herein incorporated by reference in their entirety.

Addressable arrays comprising sequences from ENZ66 can also be used to identify and characterize the temporal and tissue specific expression of ENZ66. These addressable arrays incorporate oligonucleotide sequences of sufficient length to confer the required specificity, yet be within the limitations of the production technology. The length of these probes is within a range of between about 8 to about 2000 nucleotides (or any whole number within the stated range) in length, and can partially overlap each other and/or the sequence may be represented using oligonucleotides that do not overlap. Preferably the probes consist of 60 nucleotides, and more preferably 25 nucleotides, from an ENZ66 sequence.

For example, a series of ENZ66 oligonucleotide sequences, or the complements thereof, can be used in chip format to represent all or a portion of an ENZ66 sequence. The oligonucleotides, typically between about 16 to about 40 (or any whole number within the stated range) nucleotides in length, can partially overlap each other and/or the sequence may be represented using oligonucleotides that do not overlap. Accordingly, the described polynucleotide sequences should typically comprise at least about two or three distinct oligonucleotide sequences of at least about 8 nucleotides in length of ENZ66 sequence. Such oligonucleotide sequences can begin at any nucleotide present within an ENZ66 sequence and proceed in either a sense (5'-to-3') orientation vis-a-vis the described sequences or in an antisense (3-to-5') orientation.

Microarray-based analysis allows the discovery of broad patterns of genetic activity, providing new understanding of gene functions and generating novel and unexpected insight into transcriptional processes and biological mechanisms. The use of addressable arrays comprising sequences of ENZ66 provides detailed information about ENZ66 transcriptional changes involved in a specific pathway, potentially leading to the identification of novel components or gene functions that manifest themselves as novel phenotypes.

Probes consisting of sequences of ENZ66 can also be used in the identification, selection and validation of novel molecular targets for drug discovery. The use of ENZ66 sequences permits the direct confirmation of drug targets and recognition of drug dependent changes in gene expression that are modulated through pathways distinct from the intended target of the drug. These assays can therefore be used to define and monitor both drug action and potential toxicity.

As a further example of utility, ENZ66 sequences can be utilized in microarrays or other assay formats, to screen collections of genetic material from patients who have an ENZ66-mediated disorder. These investigations can be carried out using ENZ66 sequences in silico, and by comparing previously collected genetic databases and the disclosed sequences using computer software known to those in the art. Thus ENZ66 sequences can be used to identify mutations associated with a particular disease, and also in diagnostic or prognostic assays.

In addition to the ENZ66 nucleotide sequences described above, additional full length ENZ66 cDNA or gene sequences present in the same or similar species (such as, for example, additional splice variants, polymorphisms, pseudogenes, etc.), and/or homologs or orthologs of the ENZ66 gene present in other species, can be identified and readily isolated by standard molecular biological techniques using the ENZ66 sequences presented herein. The identification of homologs of ENZ66 in related species can be useful, for example, in developing alternative animal model systems for the purpose of drug discovery.

Labeled ENZ66 nucleotide probes can also be used to screen a genomic library derived from an organism of interest, again, using appropriately stringent conditions. In particular, the identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests and clinical protocols for treating ENZ66-related disorders in human patients. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in prognostics and/or diagnostics.

Once a mutant ENZ66 sequence has been identified, it can be subject to DNA sequence analysis. By comparing the DNA sequence of the mutant ENZ66 allele to that of a corresponding normal ENZ66 allele, the mutation(s) responsible of the alteration of function of the mutant ENZ66 gene product can be ascertained.

5.2 ENZ66 Polypeptides

ENZ66 expression products, polypeptides, peptide fragments, mutated, truncated, or deleted forms of ENZ66, and/or ENZ66 fusion proteins, can be prepared for a variety of uses. These uses include, but are not limited to, the generation of antibodies, as reagents in diagnostic assays, the identification of other cellular gene products related to ENZ66, as reagents in assays for screening for compounds that can be used as pharmaceutical reagents useful in the therapeutic treatment of ENZ66-mediated diseases, including, but not limited to, hypertension, hypertension-related diseases, and complications arising from hypertension, as described herein.

The Sequence Listing discloses the amino acid sequences encoded by the described ENZ66-encoding polynucleotides. The ENZ66 sequences display initiator methionines in a DNA sequence context consistent with eucaryotic translation initiation sites.

The ENZ66 amino acid sequences of the invention include the amino acid sequences presented in the Sequence Listing, as well as analogues and derivatives thereof. Further, corresponding ENZ66 homologues from other species are encompassed by the invention. In fact, any ENZ66 protein encoded by the ENZ66 nucleotide sequences described above are within the scope of the invention, as are any novel polynucleotide sequences encoding all, or any novel portion, of an amino acid sequence presented in the Sequence Listing. The degenerate nature of the genetic code is well known, and, accordingly, each amino acid presented in the Sequence Listing is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference), are generically representative of all the various permutations and combinations of nucleic acid sequences that can encode such amino acid sequences.

The invention also encompasses proteins that are functionally equivalent to ENZ66 encoded by the presently described nucleotide sequences, as judged by any of a number of criteria, including, but not limited to, the ability to bind and modify an ENZ66 substrate, the ability to effect an identical or complementary downstream pathway, or a change in cellular metabolism (e.g., proteolytic activity, ion flux, tyrosine phosphorylation, etc.), resulting in the biological effect of ENZ66 or a change in phenotype when the ENZ66 equivalent is present in an appropriate cell type, such as altered blood pressure.

Such functionally equivalent ENZ66 proteins include, but are not limited to, additions or substitutions of amino acid residues within the amino acid sequence encoded by an ENZ66 nucleotide sequence described above, but that result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to ENZ66 DNA (using random mutagenesis techniques well-known in the art), and the resulting ENZ66 mutants tested for activity, site-directed mutations of an ENZ66 coding sequence can be engineered (using site-directed mutagenesis techniques well-known to those skilled in the art) to generate ENZ66 mutants with increased or decreased function.

For example, the novel amino acid sequence of peptides, polypeptides and proteins encoded by ENZ66 can be aligned with homologs from different species. Mutant peptides, polypeptides and proteins can be engineered so that regions of interspecies identity are maintained, whereas the variable residues are altered, e.g., by deletion or insertion of an amino acid residue(s) or by substitution of one or more different amino acid residues. For example, alterations in variable residues may be designed to produce a mutant form of an ENZ66 peptide, polypeptide or protein that is more stable but retains function. Other alterations may be designed to alter function, such as those designed to enhance binding or enzymatic activity of an ENZ66 product. One of skill in the art could easily test such mutant or deleted forms of an ENZ66 peptide, polypeptide or protein for the effect of such alterations on function using the teachings presented herein.

Other mutations to the coding sequences described herein can be made to generate peptides, polypeptides and proteins that are better suited for expression, scale up, etc., in the host cells chosen. For example, the triplet code for each amino acid can be modified to conform more closely to the preferential codon usage of the translational machinery of the particular host cell, or, for example, to yield a messenger RNA molecule with a longer half-life. Those skilled in the art would readily know what modifications of the nucleotide sequence would be desirable to conform the nucleotide sequence to preferential codon usage or to make the messenger RNA more stable. Such information would be obtainable, for example, through use of computer programs, through review of available research data on codon usage and messenger RNA stability, and through other means known to those of skill in the art.

5.2.1 ENZ66 Fusion Proteins

Peptides corresponding to one or more portions of ENZ66, truncated or deleted ENZ66, as well as fusion proteins in which the full length ENZ66, an ENZ66 peptide or truncated ENZ66 is fused to an unrelated protein are also within the scope of the invention, and can be designed on the basis of ENZ66 nucleotide and/or amino acid sequences disclosed herein. Such fusion proteins include, but are not limited to, IgFc fusions, which stabilize ENZ66 proteins or peptides and prolong half-life in vivo; fusions to any amino acid sequence that allows the fusion protein to be anchored to the cell membrane; or fusions to an enzyme, fluorescent protein, or luminescent protein that provides a marker function.

Also encompassed by the present invention are fusion proteins that direct an ENZ66 protein to a target organ and/or facilitate transport across the membrane into the cytosol. Conjugation of ENZ66 to antibody molecules or their Fab or F(ab')$_2$ fragments could be used to target cells bearing a particular epitope. Attaching the appropriate signal sequence to an ENZ66 protein would transport the protein to the desired location within the cell. Alternatively, targeting of an ENZ66 protein or its nucleic acid sequence might be achieved using liposome or lipid complex based delivery systems. Such technologies are described in "Liposomes: A Practical Approach", New, ed., Oxford University Press, NY, and in U.S. Pat. Nos. 4,594,595, 5,459,127, 5,948,767 and 6,110,490, and their respective disclosures, which are herein incorporated by reference in their entirety. Additionally embodied are novel protein constructs engineered in such a way that they facilitate transport of an ENZ66 protein to the target site or desired organ, where the protein can cross the cell and/or the nuclear membrane to a location where the protein can exert its functional activity. This goal may be achieved by, for example, coupling of an ENZ66 protein to a cytokine or other ligand that provides targeting specificity, and/or to a protein transducing domain (for examples of such transducing sequences, see generally U.S. Patent Application Ser. Nos. 60/111,701 and 60/056,713, both of which are herein incorporated by reference), to facilitate passage across cellular membranes, and can optionally be engineered to include nuclear localization sequences.

Additionally, any fusion protein may be readily purified by utilizing an antibody specific for the fusion protein being expressed. Exemplary of such purification techniques are embodiments wherein an ENZ66 sequence is subcloned into a recombination plasmid such that an ENZ66 open reading frame or a portion thereof is translationally fused to an amino-terminal tag consisting of six histidine residues (see, e.g., Janknect et al., 1991, Proc. Natl. Acad. Sci. USA 88:8972-8976). Extracts from cells expressing such a construct are loaded onto $Ni^{2+}$ nitriloacetic acid-agarose columns, and histidine-tagged proteins are selectively eluted with imidazole-containing buffers.

The novel gene products/peptide sequences encoded by ENZ66 are also useful as epitope tags for antigenic or other tagging of proteins and polypeptides that have been engineered to incorporate or comprise at least a portion of an ENZ66 peptide sequence.

5.2.2 ENZ66 Expression Systems

While ENZ66 polypeptides and peptides can be chemically synthesized (e.g., see Creighton, 1983, Proteins: Structures and Molecular Principles, W. H. Freeman & Co., NY), large polypeptides derived from ENZ66, and full length ENZ66 itself, may advantageously be produced by recombinant DNA technology using techniques well-known in the art for expressing nucleic acids containing ENZ66 gene sequences and/or coding sequences. Such methods can be used to construct expression vectors containing ENZ66 nucleotide sequences and appropriate transcriptional and translational control signals. These methods include, for example, in vitro recombinant DNA techniques, synthetic techniques, and in vivo genetic recombination (see, for example, the techniques described in Sambrook et al., 1989, supra, and Ausubel, et al., 1989, supra). Alternatively, RNA and/or DNA encoding ENZ66 nucleotide sequences may be chemically synthesized using, for example, synthesizers (see, for example, the techniques described in "Oligonucleotide Synthesis", 1984, Gait, ed., IRL Press, Oxford, which is incorporated by reference herein in its entirety).

A variety of host-expression vector systems may be utilized to express ENZ66 nucleotide sequences of the invention. Where an ENZ66 peptide or polypeptide is a soluble derivative, the peptide or polypeptide can be recovered from the host cell culture, i.e., from the host cell in cases where the ENZ66 peptide or polypeptide is not secreted, and from the culture media in cases where the ENZ66 peptide or polypeptide is secreted by the host cell. However, the expression systems also encompass engineered host cells that express ENZ66 or functional equivalents in situ, e.g., anchored in the cell membrane. Purification or enrichment of ENZ66 from such expression systems can be accomplished using appropriate detergents and lipid micelles and methods well-known to those skilled in the art. Furthermore, such engineered host cells themselves may be used in situations where it is important not only to retain the structural and functional characteristics of ENZ66, but to assess biological activity, e.g., in certain drug screening assays.

For long-term, high-yield production of recombinant proteins, stable expression is preferred. For example, cell lines that stably express any of the ENZ66 sequences described herein may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for about 1-2 days in an enriched media, and then are switched to a selective media. The selectable marker in the recombinant plasmid confers resistance to the selection, and allows cells to stably integrate the plasmid into their chromosomes and grow to form foci, which in turn can be cloned and expanded into cell lines. This method may advantageously be used to engineer cell lines that express ENZ66 gene products or portions thereof. Such engineered cell lines may be particularly useful in screening and evaluation of compounds that affect the endogenous activity of an ENZ66 protein, polypeptide or peptide.

A number of selection systems may be used, including, but not limited to, the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk⁻, hgprt⁻ or aprt⁻ cells, respectively. Also, anti-metabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre et al., 1984, Gene 30:147).

Host cells/expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing ENZ66 nucleotide sequences; yeast (e.g., *Saccharomyces, Pichia*) transformed with recombinant yeast expression vectors containing ENZ66 nucleotide sequences; insect cell systems infected with recombinant virus expression vectors (e.g., baculovirus) containing ENZ66 nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing ENZ66 nucleotide sequences; or mammalian cell systems (e.g., COS, CHO, BHK, 293, 3T3) harboring recombinant expression constructs containing ENZ66 nucleotide sequences and promoters derived from the genome of mammalian cells (e.g., metallothionein promoter) or from mammalian viruses (e.g., the adenovirus late promoter, the vaccinia virus 7.5K promoter).

In bacterial systems, a number of expression vectors may be advantageously selected depending upon the use intended for the ENZ66 gene product being expressed. For example, when a large quantity of such a protein is to be produced, for the generation of pharmaceutical compositions of ENZ66 protein or for raising antibodies to an ENZ66 protein, for example, vectors that direct the expression of high levels of fusion protein products that are readily purified may be desirable. Such vectors include, but are not limited to, the *E. coli* expression vector pUR278 (Ruther et al., 1983, EMBO J. 2:1791), in which an ENZ66 coding sequence may be ligated individually into the vector in frame with the lacZ coding region so that a fusion protein is produced; pIN vectors (Inouye and Inouye, 1985, Nucleic Acids Res. 13:3101-3109; Van Heeke and Schuster, 1989, J. Biol. Chem. 264:5503-5509); and the like. pGEX vectors may also be used to express ENZ66 polypeptides as fusion proteins with glutathione S-transferase (GST). In general, such fusion proteins are soluble and can easily be purified from lysed cells by adsorption to glutathione-agarose beads, followed by elution in the presence of free glutathione. The pGEX vectors are designed to include thrombin or factor Xa protease cleavage sites so that the cloned ENZ66 gene product can be released from the GST moiety.

In an exemplary insect system, *Autographa californica* nuclear polyhedrosis virus (AcNPV) is used as a vector to express ENZ66 sequences. The virus grows in *Spodoptera frugiperda* cells. An ENZ66 coding sequence may be cloned individually into a non-essential region (for example the polyhedrin gene) of the virus and placed under control of an AcNPV promoter (for example the polyhedrin promoter). Successful insertion of ENZ66 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted polynucleotide is expressed (e.g., see Smith et al., 1983, J. Virol. 46:584; Smith, U.S. Pat. No. 4,215,051, each incorporated herein by reference in its entirety).

In mammalian host cells, a number of viral-based expression systems may be utilized. In cases where an adenovirus is used as an expression vector, an ENZ66 nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing ENZ66 gene products in infected hosts (e.g., see Logan and Shenk, 1984, Proc. Natl. Acad. Sci. USA 81:3655-3659). Specific initiation signals may also be required for efficient translation of inserted ENZ66 nucleotide sequences. These signals include the ATG initiation codon and adjacent sequences. In cases where an entire ENZ66 gene or cDNA, including its own initiation codon and adjacent sequences, is inserted into the appropriate expression vector, no additional translational control signals may be needed. However, in cases where only a portion of an ENZ66 coding sequence is inserted, exogenous translational control signals, including, perhaps, the ATG initiation codon, may be provided. Furthermore, the initiation codon should be in phase with the reading frame of the ENZ66 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516-544).

In yeast, a number of vectors containing constitutive or inducible promoters may be used. For a review, see Ausubel et al., 1989, supra, Ch. 13; Grant et al., 1987, Methods in Enzymol. 153:516-544; Glover, 1986, DNA Cloning, Vol. II, IRL Press, Wash., D.C., Ch. 3; Bitter, 1987, Methods in Enzymol. 152:673-684; and Strathern et al., eds., "The Molecular Biology of the Yeast *Saccharomyces*", 1982, Cold Spring Harbor Press, Vols. I and II.

In cases where plant expression vectors are used, expression of the ENZ66 coding sequence may be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224: 838-843); or heat shock promoters, e.g., soybean hsp17.5-E or hsp17.3-B (Gurley et al., 1986, Mol. Cell. Biol. 6:559-565) may be used. These constructs can be introduced into plant cells using Ti plasmids, Ri plasmids, plant virus vectors, direct DNA transformation, microinjection, electroporation, etc. For reviews of such techniques see, for example, Weissbach and Weissbach, 1988, Methods for Plant Molecular Biology, Academic Press, NY, Section VIII, pp. 421-463; and Grierson and Corey, 1988, Plant Molecular Biology, 2d Ed., Blackie, London, Ch. 7-9.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct or desired modification and processing of the ENZ66 protein, polypeptide or peptide expressed. To this end, eukaryotic host cells that possess the cellular machinery for proper processing of the primary transcript, glycosylation, and phosphorylation of the ENZ66 gene product may be used. Such mammalian host cells include, but are not limited to, CHO, VERO, BHK, HeLa, COS, MDCK, 293, 3T3, WI38 and U937 cells.

5.2.3 ENZ66 Transgenic Animals

The present invention provides for transgenic animals that carry an ENZ66 transgene in all their cells, as well as animals that carry the ENZ66 transgene in some, but not all their cells, i.e., mosaic animals. Animals of any species, including, but not limited to, mice, rats, rabbits, guinea pigs, pigs, micro-pigs, goats, and non-human primates, e.g., baboons, monkeys, and chimpanzees, can be used to generate transgenic animals carrying ENZ66 polynucleotides. ENZ66 transgenes may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232-6236. The regulatory sequences required for such a cell-type specific activation will depend upon the particular cell type of interest, and will be apparent to those of skill in the art.

When it is desired that the ENZ66 transgene be integrated into the chromosomal site of the endogenous copy of the ENZ66 gene, gene targeting is preferred. Briefly, when such a technique is to be utilized, vectors containing some nucleotide sequences homologous to the endogenous ENZ66 gene are designed for the purpose of integrating, via homologous recombination with chromosomal sequences, into and disrupting the function of the nucleotide sequence of the endogenous ENZ66 gene (i.e., "knockout" animals). In this way, the expression of the endogenous ENZ66 gene may also be eliminated by inserting non-functional sequences into the endogenous ENZ66 gene. The transgene may also be selectively introduced into a particular cell type, thus inactivating the endogenous ENZ66 gene in only that cell type, by following, for example, the teaching of Gu et al., 1994, Science 265:103-106. The regulatory sequences required for such a cell-type specific inactivation will depend upon the particular cell type of interest.

Any technique known in the art may be used to introduce an ENZ66 transgene into animals to produce the founder lines of transgenic animals. Such techniques include, but are not limited to, pronuclear microinjection (U.S. Pat. No. 4,873,191, incorporated herein by reference); retrovirus-mediated gene transfer into germ lines (Van der Putten et al., 1985, Proc. Natl. Acad. Sci. USA 82:6148-6152); gene targeting in embryonic stem cells (Thompson et al., 1989, Cell 56:313-321); electroporation of embryos (Lo, 1983, Mol. Cell. Biol. 3:1803-1814); sperm-mediated gene transfer (Lavitrano et al., 1989, Cell 57:717-723); and positive-negative selection as described in U.S. Pat. No. 5,464,764, herein incorporated by reference. For a review of such techniques, see Gordon, 1989, Transgenic Animals, Intl. Rev. Cytol. 115:171-229, which is incorporated by reference herein in its entirety.

Once transgenic animals have been generated, the expression of the recombinant ENZ66 gene may be assayed utilizing standard techniques. Initial screening may be accomplished by Southern blot analysis or PCR techniques to analyze animal tissues to assay whether integration of the ENZ66 transgene has taken place. The level of mRNA expression of the ENZ66 transgene in the tissues of the transgenic animals may also be assessed using techniques that include, but are not limited to, Northern blot analysis of cell type samples obtained from the animal, in situ hybridization analysis, and RT-PCR. Samples of ENZ66-expressing tissue can also be evaluated immunocytochemically using antibodies specific for the ENZ66 transgene product, as described below.

5.3 Antibodies to ENZ66 Gene Products

Antibodies that specifically recognize one or more epitopes of ENZ66, or epitopes of conserved variants of ENZ66, or peptide fragments of ENZ66, are also encompassed by the invention. Such antibodies include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of an ENZ66 gene product in a biological sample and may, therefore, be utilized as part of a diagnostic or prognostic technique whereby patients may be tested to determine if normal or abnormal amounts of ENZ66 gene product are present. Such antibodies may also be utilized in conjunction with, for example, compound screening schemes, as described below, for the evaluation of the effect of test compounds on expression and/or activity of ENZ66 gene products. Additionally, such antibodies can be used in conjunction with the gene therapy techniques described below, for example, to evaluate the normal and/or engineered ENZ66-expressing cells prior to their introduction into a patient. Such antibodies may additionally be used in methods for the inhibition of ENZ66 activity. Thus, such antibodies may be utilized as part of ENZ66-mediated disorder treatment methods.

For the production of antibodies, various host animals may be immunized by injection with an ENZ66 protein, peptide or polypeptide, a truncated ENZ66 polypeptide, a functional equivalent of ENZ66, a mutant of ENZ66, or combinations thereof. Such host animals may include, but are not limited to, rabbits, mice, and rats, and ENZ66 knockout variants of the same, to name but a few. Various adjuvants may be used to increase the immunological response, depending on the host species, including, but not limited to, Freund's adjuvant (complete and incomplete), mineral salts such as aluminum hydroxide or aluminum phosphate, surface active substances, such as chitosan, lysolecithin, pluronic polybls, polyanions, peptides, oil emulsions, and potentially useful human adjuvants such as BCG (Bacille Calmette-Guerin) and *Corynebacterium parvum*. Alternatively, the immune response could be enhanced by combination and/or coupling with molecules such as keyhole limpet hemocyanin, tetanus toxoid, diphtheria toxoid, ovalbumin, cholera toxin, or fragments thereof. Polyclonal antibodies are heterogeneous populations of antibody molecules derived from the sera of the immunized animals.

Monoclonal antibodies, which are homogeneous populations of antibodies to a particular antigen, may be obtained by any technique that provides for the production of antibody molecules by continuous cell lines in culture. These include, but are not limited to, the hybridoma technique (Kohler and Milstein, 1975, Nature 256:495-497; and U.S. Pat. No. 4,376,110, incorporated herein in its entirety by reference), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class, including IgG, IgM, IgE, IgA, IgD, and any subclass thereof. The hybridoma producing the monoclonal antibodies of this invention may be cultivated in vitro or in vivo. Production of high titer monoclonal antibodies in vivo makes this the presently preferred method of production.

In addition, techniques developed for the production of "chimeric antibodies" (Morrison et al., 1984, Proc. Natl. Acad. Sci. USA 81:6851-6855; Neuberger et al., 1984, Nature 312:604-608; and Takeda et al., 1985, Nature 314: 452-454), by splicing the genes from a mouse antibody molecule of appropriate antigen specificity together with genes from a human antibody molecule of appropriate biological activity, can be used. A chimeric antibody is a molecule in which different portions are derived from different animal species, such as those having a variable region derived from a murine monoclonal antibody and a human immunoglobulin constant region. Such technologies are described in U.S. Pat. Nos. 6,075,181 and 5,877,397, and their respective disclosures, which are herein incorporated by reference in their entirety. Also encompassed by the present invention is the use of fully humanized monoclonal antibodies, as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 341:544-546) can be adapted to produce single chain antibodies against ENZ66 gene products or epitopes. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to, $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries may be constructed (Huse et al., 1989, Science 246:1275-1281) to allow rapid and easy identification of monoclonal Fab fragments with the desired specificity.

Antibodies to ENZ66 can, in turn, be utilized to generate anti-idiotype antibodies that "mimic" ENZ66, using techniques well-known to those skilled in the art (see, e.g., Greenspan and Bona, 1993, FASEB J. 7:437-444; and Nissinoff, 1991, J. Immunol. 147:2429-2438). For example, antibodies that bind to ENZ66 and competitively inhibit the binding of ENZ66 can be used to generate anti-idiotype antibodies that "mimic" ENZ66 protein. Such neutralizing anti-idiotype antibodies, or Fab or $F(ab')_2$ fragments of such anti-idiotype antibodies, can be used in therapeutic regimens that target ENZ66 binding partners and promote, for example, lower blood pressure.

Given the high degree of relatedness of mammalian ENZ66 proteins, the presently described knock-out mice (having never seen, and thus never been tolerized to, ENZ66) can be advantageously applied to the generation of antibodies against mammalian ENZ66 proteins (i.e., ENZ66 will be immunogenic in ENZ66 knock-out animals).

5.4 Diagnosis of ENZ66-Mediated Disorders

A variety of methods can be employed for the diagnostic and prognostic evaluation of ENZ66-mediated disorders. These methods can also be used to identify subjects having a predisposition to such disorders. Such methods may, for example, utilize reagents such as ENZ66 nucleotide sequences, ENZ66 proteins or peptides, and/or anti-ENZ66 antibodies. Specifically, such reagents may be used, for example, for: (1) the detection of the presence of ENZ66 gene mutations, or the detection of either over- or under-expression of ENZ66 mRNA relative to the non-ENZ66 disorder state; (2) the detection of either an over- or an under-abundance of ENZ66 gene product relative to the non-ENZ66 disorder state; and (3) the detection of perturbations or abnormalities in the metabolic pathways mediated by ENZ66.

The methods described herein may be performed, for example, by utilizing pre-packaged diagnostic kits comprising an ENZ66 nucleotide sequence, an ENZ66 protein or peptide and/or an ENZ66 antibody reagent described herein, which may be conveniently used, e.g., in clinical settings, to diagnose patients exhibiting or at risk of developing an ENZ66-mediated disorder, such as those caused by hypertension and/or complications arising from hypertension.

For the detection of ENZ66 mutations, any nucleated cell can be used as a starting source for genomic nucleic acid. For the detection of ENZ66 gene expression or ENZ66 gene products, any cell type or tissue in which an ENZ66 protein, polypeptide or peptide is expressed may be utilized. These techniques are described in greater detail below.

5.4.1 Detection of ENZ66 Gene Expression and Transcripts

Mutations within an ENZ66 gene can be detected by utilizing a number of techniques. Nucleic acids from any nucleated cell can be used as the starting point for such assay techniques, and may be isolated according to standard nucleic acid preparation procedures that are well-known in the art.

DNA may be used in hybridization or amplification assays of biological samples to detect abnormalities involving ENZ66 gene structure, including point mutations, insertions, deletions, and chromosomal rearrangements. Such assays may include, but are not limited to, Southern analyses, single stranded conformational polymorphism analyses (SSCP), restriction fragment length polymorphisms (RFLP, as generally described in U.S. Pat. No. 5,272,057, incorporated herein by reference), coding single nucleotide polymorphisms (cSNP), and PCR analyses.

Such diagnostic methods for the detection of ENZ66 gene-specific mutations can involve, for example, contacting and incubating nucleic acids, including recombinant DNA molecules, cloned genes, or degenerate variants thereof, obtained from a sample, e.g., derived from a patient sample or other appropriate cellular source, with one or more labeled nucleic acid reagents, including recombinant DNA molecules, cloned genes, or degenerate variants thereof, under conditions favorable for the specific annealing of these reagents to their ENZ66 complementary sequences. Preferably, the lengths of these nucleic acid reagents are at least 15 to 30 nucleotides. After incubation, all non-annealed nucleic acids are removed from the nucleic acid:ENZ66 molecule hybrid. The presence of nucleic acids that have hybridized, if any such molecules exist, is then detected. In conjunction with such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described are easily removed. Detection of the remaining, annealed, labeled ENZ66 nucleic acid reagents is accomplished using standard techniques well-known to those in the art. The ENZ66 gene sequences to which the nucleic acid reagents have annealed can be compared to the annealing pattern expected from a normal ENZ66 gene sequence in order to determine whether an ENZ66 gene mutation is present. Alternative diagnostic methods for the detection of ENZ66 gene-specific nucleic acid molecules, in patient samples or other appropriate cell sources, may involve their amplification, e.g., by PCR (the experimental embodiment set forth in U.S. Pat. Nos. 4,683,195; 4,683,202 and 4,800,159, which are incorporated herein by reference in their entirety), followed by the detection of the amplified molecules using techniques well-known to those of skill in the art. The resulting amplified sequences can be compared to those that would be expected if the nucleic acid being amplified contained only normal copies of the ENZ66 gene in order to determine whether an ENZ66 gene mutation exists.

Additionally, well-known genotyping techniques can be performed to identify individuals carrying ENZ66 gene mutations. Such techniques include, for example, the use of restriction fragment length polymorphisms (RFLPs), which involve sequence variations in one or more of the recognition sites for any particular restriction enzyme used.

Additionally, improved methods for analyzing DNA polymorphisms that can be utilized for the identification of ENZ66 gene mutations have been described that capitalize on the presence of variable numbers of short, tandemly repeated DNA sequences between certain restriction enzyme sites. For example, Weber (U.S. Pat. No. 5,075,217, which is incorporated herein by reference in its entirety) describes a DNA marker based on length polymorphisms in blocks of $(dC-dA)_n$-$(dG-dT)_n$ short tandem repeats. The average separation of $(dC-dA)_n$-$(dG-dT)_n$ blocks is estimated to be 30,000-60,000 bp. Markers that are so closely spaced exhibit a high frequency of co-inheritance, and are extremely useful in the identification of genetic mutations, such as, for example, mutations within an ENZ66 gene, and the diagnosis of diseases and disorders related to ENZ66 mutations.

Also, Caskey et al. (U.S. Pat. No. 5,364,759, which is incorporated herein by reference in its entirety) describe a DNA profiling assay for detecting short tri- and tetra-nucleotide repeat sequences. The process includes extracting the DNA of interest, amplifying the extracted DNA, and labeling the repeat sequences to form a genotypic map of the individual's DNA.

The level of ENZ66 gene expression can also be assayed by detecting and measuring ENZ66 transcription. For example, RNA from a cell type or tissue known to express, or suspected of expressing, an ENZ66 gene may be isolated and tested utilizing hybridization or PCR techniques such as those described herein. The isolated cells can be derived from cell culture or from a patient sample. The analysis of cells taken from culture may be a necessary step in the assessment of cells to be used as part of a cell-based gene therapy technique or, alternatively, to test the effect of compounds on the expression of an ENZ66 gene. Such analyses may reveal both quantitative and qualitative aspects of the expression pattern of an ENZ66 gene, including activation or inactivation of ENZ66 gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. For detection of the amplified product, the nucleic acid amplification may be performed using radioactively or non-radioactively labeled nucleotides. Alternatively, enough amplified product may be made such that the product may be visualized by utilizing standard ethidium bromide staining or any other suitable nucleic acid staining method.

Additionally, it is possible to perform such ENZ66 gene expression assays in situ, i.e., directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, "PCR In Situ Hybridization: Protocols And Applications", Raven Press, NY). Alternatively, if a sufficient quantity of the appropriate cells can be obtained, standard Northern analysis can be performed to determine the level of mRNA expression of an ENZ66 gene.

Additionally, ENZ66 oligonucleotide or polynucleotide sequences can be used as hybridization probes in conjunction with a solid support matrix/substrate (e.g., resins, beads, membranes, plastics, polymers, metal or metallized substrates, gene chips, and crystalline or polycrystalline substrates, etc.).

5.4.2 Detection of ENZ66 Gene Products

Antibodies directed against wild type or mutant ENZ66 gene products, or conserved variants or peptide fragments thereof, which are discussed above, may also be used in hypertension, and related disorders, diagnostic and prognostic assays, as described herein. Such diagnostic methods may be used to detect abnormalities in the level of ENZ66 gene expression, or abnormalities in the structure and/or temporal, tissue, cellular, or subcellular location of ENZ66, and may be performed in vivo or in vitro, such as, for example, on biopsy tissue.

For example, antibodies directed to epitopes of ENZ66 can be used in vivo to detect the pattern and level of expression of ENZ66 in the body. Such antibodies can be labeled, e.g., with a radio-opaque or other appropriate compound, and injected into a subject, in order to visualize binding to ENZ66 expressed in the body, using methods such as X-rays, CAT-scans, or MRI. Labeled antibody fragments, e.g., a Fab or single chain antibody comprising the smallest portion of the antigen binding region, may be preferred for this purpose, to promote crossing the blood-brain barrier and permit labeling of ENZ66 expressed in the brain. Additionally, any ENZ66 fusion protein or ENZ66 conjugated protein whose presence can be detected can be administered. For example, ENZ66 fusion or conjugated proteins labeled with a radio-opaque or other appropriate compound can be administered and visualized in vivo, as discussed above for labeled antibodies. Further, ENZ66 fusion proteins, such as alkaline phosphatase-ENZ66 or ENZ66-alkaline phosphatase fusion proteins, can be utilized for in vitro diagnostic procedures.

Alternatively, immunoassays or fusion protein detection assays can be utilized on biopsy and autopsy samples in vitro to permit assessment of the expression pattern of ENZ66. Such assays can include the use of antibodies directed to epitopes of any of the domains of ENZ66. The use of each or all of these labeled antibodies will yield useful information regarding translation and intracellular transport of ENZ66, and can identify alterations in processing.

The tissue or cell type to be analyzed will generally include those that are known to express, or suspected of expressing, an ENZ66 gene. The protein isolation methods employed herein may, for example, be such as those previously described (Harlow and Lane, 1988, supra). The isolated cells can be derived from cell culture or from a patient. The analysis of cells taken from culture may be a necessary step in the assessment of cells that could be used as part of a cell-based gene therapy technique or, alternatively, to test the effect of compounds on the expression of an ENZ66 gene.

For example, antibodies, or fragments of antibodies, useful in the present invention may be used to quantitatively or qualitatively detect the presence of ENZ66 gene products, or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof) or ENZ66 fusion or conjugated proteins useful in the present invention may, additionally, be employed histologically, as in immunofluorescence, immunoelectron microscopy or non-immuno assays, for in situ detection of ENZ66 gene products or conserved variants or peptide fragments thereof. In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of an ENZ66 gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for ENZ66 gene products, or conserved variants or peptide fragments thereof, will typically comprise incubating a sample, such as a biological fluid, a tissue extract, freshly harvested cells, or lysates of cells that have been incubated in cell culture, in the presence of a detectably labeled antibody capable of identifying ENZ66 gene products, or conserved variants or peptide fragments thereof, and detecting the bound antibody by any of a number of techniques well-known in the art. The biological sample may be brought in contact with and immobilized onto a solid phase support or carrier such as nitrocellulose, or other solid support that is capable of immobilizing cells, cell particles or soluble proteins. The support may then be washed with suitable buffers, followed by treatment with the detectably labeled ENZ66 antibody or ENZ66 fusion protein. The solid phase support may then be washed with the buffer a second time to remove unbound antibody or fusion protein. The amount of bound label on solid support may then be detected by conventional means.

The terms "solid phase support or carrier" are intended to include any support capable of binding an antigen or an antibody. Well-known supports or carriers include, but are not limited to, glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat, such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of ENZ66 antibody or ENZ66 fusion protein may be determined according to well-known methods. Those skilled in the art will be able to determine operative and optimal assay conditions for each determination by employing routine experimentation.

With respect to antibodies, one of the ways in which an ENZ66 antibody can be detectably labeled is by linking the same to an enzyme for use in an enzyme immunoassay (EIA; see, for example, Gosling, ed., 2000, "Immunoassays: A Practical Approach", Oxford University Press, Inc., NY). The enzyme that is bound to the antibody will react with an appropriate substrate, preferably a chromogenic substrate, in such a manner as to produce a chemical moiety that can be detected, for example, by spectrophotometric, fluorimetric or visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Additionally, detection may also be accomplished using any of a variety of other immunoassays. For example, by radioactively labeling the antibodies or antibody fragments, it is possible to detect ENZ66 through the use of a radioimmunoassay (RIA). The radioactive isotope can be detected by such means as the use of a gamma or scintillation counter, or by autoradiography.

It is also possible to label the antibody with a fluorescent compound. When the fluorescently labeled antibody is exposed to light of the proper wavelength, its presence can then be detected due to fluorescence. Exemplary fluorescent labeling compounds include, but are not limited to, fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthamide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds include, but are not limited to, luminol, isoluminol, theromatic acridinium ester, imidazole, acridinium salt and oxalate ester.

Likewise, a bioluminescent compound may be used to label the ENZ66 antibodies of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Exemplary bioluminescent compounds for purposes of labeling include, but are not limited to, luciferin, luciferase and aequorin (green fluorescent protein; as described in U.S. Pat. Nos. 5,491,084, 5,625,048, 5,777,079, 5,795,737, 5,804,387, 5,874,304, 5,968,750, 5,976,796, 6,020,192, 6,027,881, 6,054,321, 6,096,865, 6,146,826, 6,172,188 and 6,265,548, each of which is hereby incorporated by reference).

5.5 Screening Assays for Compounds that Modulate ENZ66 Expression or Activity

The following assays are designed to identify compounds that interact with (e.g., bind to) ENZ66, compounds that interact with (e.g., bind to) intracellular proteins that interact with ENZ66, compounds that interact with (e.g., bind to) both intracellular and extracellular proteins or receptors that regulate ENZ66 activity and expression, compounds that interfere with the interaction of ENZ66 or proteins or compounds involved in ENZ66-mediated activity, and compounds that modulate the activity of ENZ66 gene (i.e., modulate the level of ENZ66 gene expression) or modulate the level of ENZ66. Assays may additionally be utilized that identify compounds that bind to ENZ66 gene regulatory sequences (e.g., promoter sequences) and that may modulate ENZ66 gene expression.

The compounds that can be screened in accordance with the present invention include, but are not limited to, peptides, antibodies and fragments thereof, and other organic compounds (e.g., peptidomimetics, small organic compounds) that bind to ENZ66 and either mimic or increase the activity of ENZ66 (i.e., agonists) or inhibit the activity of ENZ66 (i.e., antagonists); as well as peptides, antibodies or fragments thereof, and other organic compounds that mimic or increase ENZ66 activity or inhibit the activity of ENZ66.

Such compounds may include, but are not limited to, peptides such as, for example, soluble peptides, including, but not limited to, members of random peptide libraries (see, e.g., Lam et al., 1991, Nature 354:82-84; Houghten et al., 1991, Nature 354:84-86), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., 1993, Cell 72:767-778), antibodies (including, but not limited to, polyclonal, monoclonal, humanized, anti-idiotypic, chimeric or single chain antibodies, and Fab, F(ab')$_2$ and Fab expression library fragments, and epitope-binding fragments thereof), and small organic or inorganic molecules.

Other compounds that can be screened in accordance with the invention include, but are not limited to, small organic molecules that are able to gain entry into an appropriate cell and affect the expression of an ENZ66 gene, or some other gene involved in an ENZ66 pathway (e.g., by interacting with the regulatory region or transcription factors involved in gene expression); or such compounds that affect the activity of ENZ66 or the activity of some other intracellular factor involved in an ENZ66 pathway.

Computer modeling and searching technologies permit identification of compounds, or the improvement of already identified compounds, that can modulate ENZ66 expression or activity. Having identified such a compound or composition, the active sites or regions are identified. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method can be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or a combination thereof, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. The compounds found from such a search are potential ENZ66 modulating compounds.

Alternatively, these methods can be used to identify improved modulating compounds from an already known modulating; compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of ENZ66, and related transduction and transcription factors, will be apparent to those of skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988, Acta Pharmaceutical Fennica 97:159-166; Ripka, New Scientist 54-57 (Jun. 16, 1988); McKinaly and Rossmann, 1989, Ann. Rev. Pharmacol. Toxiciol. 29:111-122; Perry and Davies, OSAR: Quantitative Structure-Activity Relationships in Drug Design, pp. 189-193 (Alan R. Liss, Inc. 1989); Lewis and Dean, 1989 Proc. R. Soc. Lond. 236:125-140 and 141-162; and, with respect to a model receptor for nucleic acid components, Askew, et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific, to particular proteins, they can be adapted to the design of drugs specific to regions of DNA or RNA, once that region is identified.

Although described above with reference to design and generation of compounds that could alter binding, one could also screen libraries of known compounds, including natural products or synthetic chemicals, and biologically active materials, including proteins, for compounds that are inhibitors or activators of ENZ66.

Compounds identified via assays such as those described herein may be useful, for example, in further elaborating the biological function of an ENZ66 gene product, and for ameliorating hypertension and related disorders.

5.5.1 In Vitro Screening Assays for Compounds that Bind to ENZ66

In vitro systems may be designed to identify compounds capable of interacting with (e.g., binding to) ENZ66. The compounds thus identified (such as ENZ66 modulators, natural ENZ66 substrates, etc.) can be useful, for example, in modulating the activity of wild type and/or mutant ENZ66 gene products; in elaborating the biological function of ENZ66; in screens for identifying compounds that disrupt normal ENZ66 interactions; or in themselves directly disrupt such interactions.

The principle of the assays used to identify compounds that bind to ENZ66 involves preparing a reaction mixture of ENZ66 and the test compound under conditions and for a time sufficient to allow the two components to interact and bind, thus forming a complex that can be removed and/or detected in the reaction mixture. The ENZ66 species used can vary depending upon the goal of the screening assay. For example, where agonists of the natural ligand/substrate are sought, full length ENZ66, or a soluble truncated ENZ66 polypeptide that affords advantages in the assay system (e.g., labeling, isolation of the resulting complex, etc.) can be utilized.

The screening assays can be conducted in a variety of ways. For example, one method to conduct such an assay would involve anchoring an ENZ66 protein, polypeptide, peptide, or fusion protein, or the test substance, onto a solid phase and detecting ENZ66/test compound complexes anchored on the solid phase at the end of the reaction. In one embodiment of such a method, the ENZ66 reactant may be anchored onto a solid surface, and the test compound, which is not anchored, may be labeled, either directly or indirectly. Examples of some of the technologies available to immobilize the molecules are discussed in Cass, ed., "Immobilized Biomolecules In Analysis: A Practical Approach", Oxford University Press, NY.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected, e.g., using an immobilized antibody specific for ENZ66 protein, polypeptide, peptide, fusion protein, or the test compound, to anchor any complexes formed in solution, and a labeled antibody specific for the other component of the possible complex to detect anchored complexes.

Alternatively, cell-based assays can be used to identify compounds that interact with ENZ66. To this end, cell lines that express ENZ66, or cell lines (e.g., COS cells, CHO cells, fibroblasts, etc.) that have been genetically engineered to express ENZ66 (e.g., by transfection or transduction of ENZ66 DNA) can be used.

5.5.2 Assays for Proteins that Interact with ENZ66

As ENZ66 has enzyme activity as a kinase, methods common to and well-known in the art for the study of enzymes, particularly kinases, and protein function may be used to characterize ENZ66 function and activity. These methods are well-known to those in the art. In addition, any method suitable for detecting protein-protein interactions may be employed for identifying proteins that interact with ENZ66. Among the traditional methods that may be employed are co-immunoprecipitation, crosslinking and co-purification through gradients or chromatographic columns of cell lysates, or proteins obtained from cell lysates, and ENZ66 to identify proteins in the lysate that interact with ENZ66. For these assays, the ENZ66 component used can be a full length ENZ66, a peptide or polypeptide corresponding to one or more domains of ENZ66, or a fusion protein containing one or more domains of ENZ66. Once isolated, such an intracellular protein can be identified and can, in turn, be used in conjunction with standard techniques to identify proteins with which it interacts. For example, at least a portion of the amino acid sequence of an intracellular protein that interacts with ENZ66 can be ascertained using techniques well-known to those of skill in the art, such as via the Edman degradation technique (see, e.g., Creighton, 1983, supra, pp. 34-49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and screening are well-known (see, e.g., Ausubel, supra., and Innis et al., eds. "PCR Protocols: A Guide to Methods and Applications", 1990, Academic Press, Inc., NY).

Additionally, methods may be employed that result in the simultaneous identification of genes that encode proteins that are capable of interacting with ENZ66. These methods include, for example, probing expression libraries, in a manner similar to the well-known technique of antibody probing of lambda gt11 libraries, using a labeled ENZ66 protein, polypeptide, peptide or fusion protein, e.g., an ENZ66 polypeptide or ENZ66 domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One version of this system utilizes yeast cells (Chien et al., 1991, Proc. Natl. Acad. Sci. USA, 88:9578-9582), while another uses mammalian cells (Luo et al., 1997, Biotechniques 22:350-352). Both the yeast and mammalian two-hybrid systems are commercially available from Clontech (Palo Alto, Calif.), and are further described in U.S. Pat. Nos. 5,283,173, 5,468,614, and 5,667,973, which are herein incorporated by reference in their entirety.

Briefly, utilizing such a system, plasmids are constructed that encode two hybrid proteins: one plasmid consists of nucleotides encoding the DNA-binding domain of a transcription activator protein fused to an ENZ66 nucleotide sequence encoding a ENZ66 protein, polypeptide, peptide or fusion protein, and the other plasmid consists of nucleotides encoding an activation domain of a transcription activator protein fused to a cDNA encoding an unknown protein to be tested for interaction with ENZ66, which has been recombined into this plasmid as part of a cDNA library. The DNA-binding domain fusion plasmid and the cDNA library are transformed into a strain of the yeast *Saccharomyces cerevisiae* or a mammalian cell (such as Saos-2, CHO, CV1, Jurkat or HeLa) that contains a reporter gene (e.g., HBS, lacZ, CAT or a gene encoding an essential amino acid synthetase) whose regulatory region contains the binding site of the transcription activator. Either hybrid protein alone cannot activate transcription of the reporter gene: the DNA-binding domain hybrid cannot because it does not provide activation function; and the activation domain hybrid cannot because it cannot localize to the binding site of the activator. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, ENZ66 may be used as the bait gene product. Total genomic or cDNA sequences are fused to DNA encoding an activation domain. This library and a plasmid encoding a hybrid of a bait ENZ66 gene product fused to the DNA-binding domain are co-transformed into a reporter strain, and the resulting transformants are screened for those that express the reporter gene. For example, and not by way of limitation, a bait ENZ66 sequence, such as an open reading frame of ENZ66 (or a domain of ENZ66) can be cloned into a vector such that it is translationally fused to DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait ENZ66 gene product are to be detected can be made using methods routinely practiced in the art. According to one particular system, for example, the cDNA fragments can be inserted into a vector such that they are translationally fused to the transcriptional activation domain of GAL4. This library can be co-transformed along with the bait ENZ66 gene-GAL4 fusion plasmid into a yeast strain that cannot grow without added histidine, and that contains a HIS3 gene driven by a promoter that contains GAL4 activation sequence. A cDNA encoded protein, fused to GAL4 transcriptional activation domain, which interacts with bait ENZ66 gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait ENZ66 gene-interacting protein using techniques routinely practiced in the art.

5.5.3 Assays for Compounds that Interfere with ENZ66 Activity

The macromolecules that interact with ENZ66 are referred to, for purposes of this discussion, as "binding partners". These binding partners are likely to be involved in an ENZ66 pathway, and therefore, may have a role in ENZ66-mediated disorders. Therefore, it is desirable to identify compounds that interfere with or disrupt the interaction of such binding partners with ENZ66, and that may be useful in regulating the activity of ENZ66 and controlling ENZ66-mediated disorders.

The basic principle of the assay systems used to identify compounds that interfere with the interaction between ENZ66 and its binding partner or partners involves preparing a reaction mixture containing ENZ66 protein, polypeptide, peptide or fusion protein, and the binding partner under conditions and for a time sufficient to allow the components to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the ENZ66 moiety and its binding partner(s). Control reaction mixtures are incubated without the test compound or with a placebo. The formation of complexes between the ENZ66, moiety and the binding partner is then detected. The formation of a complex in the control reaction, but not in the reaction mixture containing the test compound, indicates that the compound interferes with the interaction of ENZ66 and the interactive binding partner. Additionally, complex formation within reaction mixtures containing the test compound and normal ENZ66 protein may also be compared to complex formation within reaction mixtures containing the test compound and a mutant ENZ66. This comparison may be important in those cases wherein it is desirable to identify compounds that disrupt interactions of mutant but not normal ENZ66.

Assays for compounds that interfere with the interaction of ENZ66 and binding partner(s) can be conducted in a heterogeneous or homogeneous format. Heterogeneous assays involve anchoring either the ENZ66 moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance, i.e., by adding the test substance to the reaction mixture prior to or simultaneously with the ENZ66 moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the ENZ66 moiety or the interactive binding partner is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of an ENZ66 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing), and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface, e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected, e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. In this approach, a preformed complex of an ENZ66 moiety and the interactive binding partner is prepared in which either ENZ66 or its binding partner is labeled, but the signal generated by the label is quenched due to formation of the complex (see, e.g., U.S. Pat. No. 4,109,496, incorporated herein by reference, which utilizes this approach for immunoassays). The addition of a test substance that competes with and displaces one of the species from the preformed complex will result in the generation of a signal above background. In this way, test substances that disrupt ENZ66/intracellular binding partner interactions can be identified.

In a particular embodiment, an ENZ66 fusion protein can be prepared for immobilization. For example, ENZ66, or a peptide fragment thereof, e.g., corresponding to one or more particular domain(s), can be fused to glutathione-S-transferase (GST) using a fusion vector, such as pGEX-5X-1, in such a manner that the GST binding activity is maintained in the resulting fusion protein. An interactive binding partner, identified as described herein, can be purified and used to raise polyclonal and monoclonal antibodies, using methods routinely practiced in the art. Such antibodies can be labeled with a radioactive isotope, $^{125}$I for example, by methods routinely practiced in the art. In a heterogeneous assay, such GST-ENZ66 fusion proteins can be anchored to glutathione-agarose beads. The interactive binding partner can then be added in the presence or absence of the test compound in a manner that allows interaction and binding to occur. At the end of the reaction period, unbound material can be washed away, and a labeled monoclonal antibody that binds the binding partner can be added to the system and allowed to bind to complexed binding partner. The interaction between ENZ66 and the interactive binding partner can be detected by measuring the amount of radioactivity that remains associated with the glutathione-agarose beads. A successful inhibition of the interaction by the test compound will result in a decrease in measured radioactivity.

Alternatively, a GST-ENZ66 fusion protein and an interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the ENZ66/binding partner interaction can be detected by adding a labeled antibody against the binding partner and measuring the radioactivity associated with the beads.

In another embodiment of the invention, where the binding partner is a protein, these same techniques can be employed using peptide fragments that correspond to one or more of the binding domains of ENZ66 and/or the interactive binding partner, in place of one or both of the full length proteins. Any number of methods routinely practiced in the art can be used to identify and isolate the binding domains or regions. These methods include, but are not limited to, mutagenesis of the gene encoding one of the proteins, and screening for disruption of binding in a co-immunoprecipitation assay. Compensating mutation(s) in the sequence encoding the second species in the complex can then be selected. Sequence analysis of the sequences encoding the respective proteins will reveal the mutation(s) that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once a sequence encoding the binding partner is obtained, short polynucleotide segments can be engineered to express peptide fragments of the protein, which can then be tested for binding activity, and purified or synthesized.

For example, and not by way of limitation, an ENZ66 protein, polypeptide or peptide can be anchored to a solid material, as described above, by making a GST-ENZ66 fusion protein and allowing it to bind to glutathione agarose beads. The interactive binding partner can be labeled with a radioactive isotope, such as $^{35}S$, and cleaved with a proteolytic enzyme, such as trypsin. Cleavage products can then be added to the anchored GST-ENZ66 fusion protein and allowed to bind. After washing away unbound peptides, labeled bound material, representing the intracellular binding partner binding domain, can be eluted, purified, and analyzed to determine the amino acid sequence by well-known methods. Peptides so identified can be produced synthetically or fused to appropriate facilitative proteins using recombinant DNA technology.

5.5.4 the Use of Compounds to Treat ENZ66-Mediated Disorders

The invention also encompasses the use of agonists and antagonists of ENZ66 (including small molecules and large molecules), mutant versions of ENZ66 or portions thereof that compete with native ENZ66, peptides, and antibodies, as well as nucleotide sequences that can be used to inhibit the expression of ENZ66 (e.g., antisense and ribozyme molecules, and gene or regulatory sequence replacement constructs) or to enhance the expression of ENZ66 polynucleotides (e.g., expression constructs that place the described polynucleotide under the control of a strong promoter system) in the treatment of ENZ66-mediated disorders. Compounds including, but not limited to, those identified via assay techniques such as those described above, can be tested for the ability to ameliorate symptoms associated with ENZ66-mediated disorders, including those involving hypertension and complications associated with hypertension.

The assays described above can identify compounds that affect ENZ66 activity, or compounds that affect ENZ66 gene activity (by affecting ENZ66 gene expression, including molecules, e.g., proteins or small organic molecules, that affect or interfere with splicing events so that expression of a full length or a truncated form of ENZ66 can be modulated). However, it should be noted that the assays described can also be used to identify compounds that indirectly modulate ENZ66. The identification and use of compounds that affect an ENZ66 independent step in an ENZ66 pathway are also within the scope of the invention. Compounds that indirectly affect ENZ66 activity can also be used as part of a therapeutic method for the treatment of ENZ66-mediated disorders.

The invention additionally encompasses cell-based and animal model-based assays for the identification of compounds exhibiting an ability to ameliorate the symptoms of ENZ66-mediated disorders. Cell-based systems used to identify compounds that may act to ameliorate ENZ66-mediated disorder symptoms can include, for example, recombinant or non-recombinant cells, such as cell lines that express an ENZ66 sequence. Host cells (e.g., COS cells, CHO cells, fibroblasts) genetically engineered to express a functional ENZ66 can also be used. The presence of a functional ENZ66 can be determined, for example, by a chemical or a phenotypic change, the induction of another host cell gene, a change in ion flux (e.g., $Ca^{++}$), or tyrosine phosphorylation of host cell proteins, etc.

In utilizing such cell systems, cells may be exposed to a compound suspected of exhibiting an ability to ameliorate the symptoms of ENZ66-mediated disorders, at a sufficient concentration and for a time sufficient to elicit such an amelioration of the symptoms of ENZ66-mediated disorders in the exposed cells. After exposure, the cells can be assayed to measure alterations in ENZ66 expression, e.g., by assaying cell lysates for ENZ66 mRNA transcripts (e.g., by Northern analysis or RT-PCR), or by assaying for the level of ENZ66 protein expressed in the cell (e.g., by SDS-PAGE and Western blot or immunoprecipitation); compounds that regulate or modulate ENZ66 expression are good candidates as therapeutics. Alternatively, the cells can be examined to determine whether one or more ENZ66 disorder-like cellular phenotype has been altered to resemble a more normal or more wild type, non-ENZ66 disorder phenotype, or a phenotype more likely to produce a lower incidence or severity of disorder symptoms. Still further, the expression and/or activity of components of the signal transduction pathway(s) of which ENZ66 is a part, or the activity of an ENZ66 signal transduction pathway itself, can be assayed.

In addition, animal-based ENZ66-mediated disorder systems may be used to identify compounds capable of treating or ameliorating symptoms associated with ENZ66-mediated disorders. These animals may be transgenic, knockout, or knock-in (preferably humanized knock-ins where, for example, the endogenous animal ENZ66 gene has been replaced by a human ENZ66 sequence) animals, as described herein. Such animal models may be used as test substrates for the identification of drugs, pharmaceuticals; therapies and interventions that may be effective in treating such disorders. For example, animal models can be exposed to a compound suspected of exhibiting an ability to ameliorate symptoms of ENZ66-mediated disorders, at a sufficient concentration and for a time sufficient to elicit such an amelioration of ENZ66 disorder associated symptoms in the exposed animals. The response of the animals to the exposure may be monitored by assessing the reversal of symptoms associated with ENZ66-mediated disorders. With regard to intervention, any treatments that reverse, halt or slow the progression of any aspect of symptoms associated with ENZ66 disorders should be considered as candidates for therapeutic intervention in treatment of human ENZ66 disorders. Dosages of test agents may be determined by deriving toxicity and dose-response curves.

5.6 Kinase Assays

The activity of ENZ66 can be determined or measured using any standard kinase assay, many examples of which will be well-known to those of skill in the art. In addition to the specific assays described herein elsewhere, the following assays are exemplary of additional kinase assays that can be used with ENZ66 sequences described herein.

A coupled spectrophotometric assay can be used in which ADP generated by ENZ66 is converted to ATP by pyruvate kinase (PK) with the concomitant production of pyruvate from phosphoenolpyruvate (PEP). Lactate dehydrogenase (LDH) reduces pyruvate to lactate with the oxidation of NADH. NADH production is monitored at 340 nm using a microplate reader for 20 min at 30° C. Reactions are carried out in 100 mM HEPES, pH 7.6, 10 mM MgCl$_2$, and started by addition of 100 mM ATP. Pyruvate kinase (100 mg/ml), LDH (50 mg/ml), PEP (2 mM) and NADH (140 mM) are added in large excess. Addition of 200 mM of a peptide substrate allows measurement of kinase activity.

In $K_i$ determinations, ENZ66 and an inhibitor are pre-incubated for 15 min at 30° C. prior to assay by addition of ATP. Inhibition constants are determined by fitting kinetic data to the Morrison tight-binding equation (Morrison et al., 1988, Adv. Enzymol. Relat. Areas Mol. Biol. 61:201-301) using KineTic (BioKin, 1992). $^{32}$P incorporation into substrate (0.1 mg/ml) by 7.5 nM ENZ66 is assayed for 10 min at 30° C. in 50 mM HEPES, pH 7, 10 mM MgCl$_2$ and 2 mM DTT, and visualized by autoradiography.

Additional kinase assays are described in U.S. Pat. No. 5,958,713, and in Williams and Cole (2001, Trends in Biochemical Science 26:271-273), and the references therein, each of which are specifically incorporated herein by reference in their entirety.

5.6.1 Low Throughput ENZ66 Kinase Assay

An exemplary low throughput ENZ66 kinase assay using a synthetic peptide as the substrate is performed according to Ausubel et al. (1989, supra) with slight modifications. The assay contains 50 mM Tris/HCl, pH 7.3, 2 mM DTT, 10 mM MgCl$_2$, 5 mg/ml BSA, 0.1 mM [γ-P$^{32}$]ATP (5 mCi), various amounts of kinase, and various concentrations of a synthetic peptide, in a total of 50 μl. The assay is carried out at 30° C., and started with the addition of the kinase. After the desired incubation time (usually 15 min), the reaction is terminated by adding 50 μl ice-cold 20% TCA to precipitate the proteins, but not the peptide. After spinning for 2 minutes in a microcentrifuge, 60 μl of the supernatant fractions are spotted onto Whatman P81 cellulose phosphate filter circles. The P81 filter circles are then washed three times with 0.5% cold phosphoric acid (5-10 minutes per wash) and once with 100 ml 95% ethanol at room temperature. The filter circles are allowed to dry at room temperature for 5 minutes before they are transferred into scintillation vials. The $^{32}$P incorporation is measured by counting the dried pads in a scintillation counter. The specific activity of ATP in a kinase reaction (e.g., in cpm/pmol) is determined by spotting a small sample (2-5 μl) of the reaction onto a P81 filter circle and counting directly (no washing). Counts per minutes (cpm) obtained in the kinase reaction (minus blank) are then divided by the specific activity to determine the moles of phosphate transferred in the reaction.

Protein phosphorylation by ENZ66 is measured in a different way than peptide phosphorylation, since certain aspects of the filter assays described above are not suitable for protein substrates. Incubation of a protein substrate with the ENZ66 enzyme is performed as described above, except in a total volume of 25 μl, but the reaction is stopped by adding 25 μl of polyacrylamide gel electrophoresis (PAGE) loading buffer containing SDS (0.25 M Tris-HCl pH 6.8, 2% SDS, 15% glycerol, 0.1 mg/ml bromphenol blue and 2.5% (v/v) β-mercaptoethanol), and heating to 95° C. for 5 minutes. An aliquot (10 to 20 μl) of the mixture is then electrophoresed on a 12% SDS-PAGE gel. ENZ66-specific-phosphorylation is detected and quantified by standard radiography using appropriate control samples.

The Vm/Km kinetics of various peptide substrates for ENZ66 is determined essentially by using a variation of the protocol above. The amount of enzyme needed for kinetic experiments is determined by verifying that the protein phosphorylation is proportional to the enzyme concentration under the condition of the assay. Phosphorylation of peptides should also be linear with time, and for measurements of kinetic constants, only the initial rates of the reactions are used. Controls to determine the background signals (no enzyme, and/or no substrate) are routinely included. Assuming saturation with ATP, a wide variation of peptide concentration allows the determination of Vm and Km for the kinase by fitting v=Vm*s/(Km+s) directly in the hyperbolic form to the experimental phosphate transfer data. In the case of substrate inhibition, the following equation is used: v=Vm*s/(Km+s+s$^2$/Ki). The kinetic efficiencies for different peptides are calculated by the Vm/Km ratio.

5.6.2 High Throughput ENZ66 Kinase Assay

An exemplary high throughput screening assay for ENZ66 is described using two different microplate homogeneous assay approaches, the Scintillation Proximity Assay (Amersham Pharmacia Biotech, Piscataway, N.J.) and the FlashPlate (Perkin Elmer, Boston, Mass.) assay. In both formats the kinase substrate is a biotinylated peptide. A known kinase or ENZ66 protein is added along with substrate peptide (2 μM), $^{33}$P-ATP (0.1 uCi/10 μM) and Mg$^{++}$ (5 mM) and incubated in the presence of 50 mM Tris buffer at pH 7.4. After 30 minutes, the reaction is terminated by adding an equal volume of stop buffer (50 mM of EDTA, 100 μM of ATP, 50 mM Tris). Phosphorylated and non-phosphorylated peptide substrate is allowed to bind, depending on the assay format, to either the streptavidin-labeled FlashPlate or streptavidin-labeled beads for the Scintillation Proximity Assay. In the FlashPlate assay format, the wells are subsequently washed thrice with stop buffer, sealed, and the amount of $^{33}$P-ATP incorporated into the bound biotinylated substrate is determined using a microplate scintillation counter (TopCount, Packard Bioscience, Meriden, Conn.). In the Scintillation Proximity Assay format, beads in sealed plates are allowed to settle overnight and the amount of $^{33}$P-ATP incorporated into the bound biotinylated substrate peptide is determined using the microplate scintillation counter.

To assay for potential kinase inhibitor activity, a test compound is added to the mixture described above of ENZ66 protein or a known kinase, the substrate peptide (2 µM), $^{33}$P-ATP (0.1 µCi/10 µM) and Mg$^{++}$ (5 mM), and the mixture is incubated in the presence of 50 mM Tris buffer at pH 7.4. After 30 minutes, the reaction is terminated with equal volume of stop buffer (50 mM of EDTA, 100 µM of ATP, 50 mM Tris). Phosphorylated and non-phosphorylated peptide substrate is allowed to bind, depending on the assay format, to either the streptavidin-labeled FlashPlate or streptavidin-labeled beads for the Scintillation Proximity Assay. In the FlashPlate assay format, the wells are subsequently washed thrice with stop buffer, sealed and the amount of $^{33}$P-ATP incorporated into the bound biotinylated substrate peptide is determined using the microplate scintillation counter. In the Scintillation Proximity Assay format, beads in sealed plates are allowed to settle overnight and the amount of $^{33}$P-ATP incorporated into the bound biotinylated substrate peptide is determined using the microplate scintillation counter. Maximum (wells without inhibitor) and minimum (wells without enzyme) activity controls are included in each 96-well plate. The inhibitory activity of each compound is estimated using the formula:

(1−((compound well−average of minimum wells)/
(average of maximum wells−average of minimum wells)))

5.7 Pharmaceutical Preparations and Methods of Administration

Compounds that are determined to affect expression of the sequences of the current invention, or the interaction of the peptides and proteins of the present invention with any of their binding partners, can be administered to a patient at therapeutically effective doses to treat or ameliorate hypertension and/or complications arising from hypertension. A therapeutically effective dose refers to that amount of the compound sufficient to result in any delay in onset, amelioration or retardation of disease symptoms.

5.7.1 Effective Dose

Toxicity and therapeutic efficacy of such compounds can be determined by standard pharmaceutical procedures in cell cultures or experimental animals, e.g., for determining the LD$_{50}$ (the dose lethal to 50% of the population) and the ED$_{50}$ (the dose therapeutically effective in 50% of the population). The dose ratio between toxic and therapeutic effects is the therapeutic index, and it can be expressed as the ratio LD$_{50}$/ED$_{50}$. Compounds that exhibit large therapeutic indices are preferred. Compounds that exhibit toxic side effects may be used in certain embodiments, however care should usually be taken to design delivery systems that target such compounds preferentially to the site of affected tissue, in order to minimize potential damage to uninfected cells and, thereby, reduce side effects.

The data obtained from cell culture assays and animal studies can be used in formulating a range of dosages for use in humans. The dosages of such compounds lie preferably within a range of circulating concentrations that include the ED$_{50}$ with little or no toxicity. The dosage may vary within this range depending upon the dosage form employed and the route of administration utilized. For any compound used in the methods of the invention, the therapeutically effective dose can be estimated initially from cell culture assays. A dose may be formulated in animal models to achieve a circulating plasma concentration range that includes the IC$_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

When the therapeutic treatment of disease is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly extrapolate doses for efficacy and avoiding toxicity to other species, including human. Before human studies of efficacy are undertaken, Phase I clinical studies in normal subjects help establish safe doses.

Additionally, the bioactive agent may be complexed with a variety of well established compounds or structures that, for instance, enhance the stability of the bioactive agent, or otherwise enhance its pharmacological properties (e.g., increase in vivo half-life, reduce toxicity, etc.).

The therapeutic agents will be administered by any number of methods known to those of ordinary skill in the art including, but not limited to, inhalation; subcutaneous (sub-q); intravenous (I.V.); intraperitoneal (I.P.); intramuscular (I.M.), or intrathecal injection; or topically applied (transderm, ointments, creams, salves, eye drops, and the like).

5.7.2 Formulations and Use

Pharmaceutical compositions for use in accordance with the present invention may be formulated in conventional manners using one or more physiologically acceptable carriers or excipients.

Thus, the compounds and their physiologically acceptable salts and solvates may be formulated for administration by inhalation or insufflation (either through the mouth or the nose), or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or, hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring agents, coloring agents and sweetening agents as appropriate.

Preparations for oral administration may be suitably formulated to give controlled release of the active compound. For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated as compositions for rectal administration such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil), ion exchange resins, or as sparingly soluble derivatives, for example, as a sparingly soluble salt. The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

The examples below are provided to illustrate the subject invention. These examples are provided by way of illustration only, and are not included for the purpose of limiting the invention in any way whatsoever.

6.0 EXAMPLES

6.1 ENZ66 Gene Disrupted Mice

Gene trapping is a method of nonspecific insertional mutagenesis that uses a fragment of DNA coding for a reporter or selectable marker gene as a mutagen. Gene trap vectors have been designed to integrate into introns or exons in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells derived from murine strain A129) were mutated by a process involving the insertion of at least a portion of a genetically engineered vector sequence into the ENZ66 gene. The mutated embryonic stem cells were then microinjected into blastocysts, which were subsequently introduced into pseudopregnant female hosts and carried to term using established methods, such as those described in, for example, Zambrowicz et al., eds., "Mouse Mutagenesis", 1998, Lexicon Press, The Woodlands, Tex., and periodic updates thereof, herein incorporated by reference. In this case, the virus inserted between exons 1 and 2, and disrupted the ENZ66 gene. The resulting chimeric animals were subsequently bred to produce offspring capable of germline transmission of an allele containing the engineered mutation in the ENZ66 gene.

Techniques useful to disrupt a gene in a cell, and especially an ES cell, that may already have a disrupted gene are disclosed in U.S. Pat. Nos. 6,136,566, 6,139,833 and 6,207,371, and U.S. patent application Ser. No. 08/728,963, each of which are hereby incorporated herein by reference in their entirety.

6.1.1 the Effect of ENZ66 Disruption on Mouse Physiology

Mice homozygous for the disruption of the ENZ66 gene appear to be mid-gestational lethal. Heterozygous females were time mated, and embryos were harvested at different stages of development. Depending on the embryonic stage of development, the yolk sac or embryonic tail is used for genotyping. Resorption moles, which indicate very early embryonic lethality, are also collected and counted for each litter. Resorption moles are not genotyped. No homozygous (−/−) ENZ66 embryos studied survived past day 13 of gestation.

For gross morphology studies, embryos were collected at different developmental stages, photographed, and evaluated for neural tube, skeletal defects, developmental delay and overall size or shape differences. Typically, a stereoscope is used to evaluate the embryos and digitally capture the embryo images. Additionally, embryos are studied histologically. Formalin fixed embryos are dissected mid-sagittally, processed, and paraffin embedded. Five micron thick sections are cut and stained with hematoxylin and eosin. Sections of mutants, heterozygotes and wild type litter mates are evaluated microscopically. By gross morphology and histology, the heterozygous (+/−) and wild-type (+/+) embryos appear normal.

Thus, for the remaining studies, mice heterozygous for the disruption of the ENZ66 gene were studied in conjunction with wild-type litter mates. During this analysis, the mice were subjected to a medical work-up using an integrated suite of medical diagnostic procedures designed to assess the function of the major mammalian organ systems in the subject. By studying numerous mice in which the ENZ66 gene had been disrupted, in conjunction with wild-type litter mates, more reliable and repeatable data was obtained.

Disruption of the ENZ66 gene resulted in an unexpected reduction in blood pressure, as described in greater detail below.

The disruption of the ENZ66 gene was confirmed by Southern analysis. OMNIBANK Sequence Tag #38262 lines up with exon 2 using SEQUENCHER, implying that the retrovirus vector inserted between exons 1 and 2 of the ENZ66 gene.

Additional studies of the expression patterns of human and murine ENZ66 showed that ENZ66 can be detected in many mouse and human tissues by RT-PCR. ENZ66 transcripts were detected in mouse tissue derived from mouse brain, thymus, spleen, lung, kidney, liver, testis, salivary gland, stomach, small intestine, colon, skeletal muscle, heart, uterus, adipose, bladder, ovary, gall bladder, lymph node, cerebellum, esophagus, prostate, tongue, thyroid, bone marrow, spinal cord, trachea, aorta, whole blood, eye, pituitary gland, skin, nasal epithelium, whole bone (femur), mammary gland, placenta, 9.5 day embryo, 12.5 day embryo, fetal brain, fetal lung, and fetal liver.

ENZ66 transcripts were detected in human tissue derived from human fetal brain, brain, pituitary, cerebellum, spinal cord, thymus, spleen, lymph node, bone marrow, trachea, lung, kidney, fetal liver, liver, prostate, testis, thyroid, adrenal gland, pancreas, salivary gland, stomach, small intestine, colon, skeletal muscle, heart, uterus, placenta, mammary gland, adipose, skin, esophagus, bladder, cervix, rectum, pericardium, eye, ovary, fetal kidney, fetal lung, gall bladder, tongue, aorta, embryo (6, 9 and 12 weeks), adenocarcinoma (adrenal cortex), osteosarcoma, embryonic carcinoma, umbilical vein, and microvascular endothelium.

6.1.2 Size, Percent Body Fat, and Bone Mineral Density of ENZ66 Knockouts

Body composition and percent body fat was measured by dual energy X-ray absorptiometry (DEXA) using the Piximus small animal densitometer (Lunar Corporation, Madison, Wis.). Individual mice were sedated with Avertin (1.25% solution, 2.5 mg/10 gm body weight delivered by intraperitoneal injection), immobilized on a positioning tray and then placed on the Piximus imaging window. All scans were performed using the total body mode (0.18×0.18 mm), and the analysis was performed on the total body region of interest. The entire body, except the head, of each mouse was exposed for 5 minutes to a cone shaped beam of both high and low energy x-rays. A high-resolution digital picture was taken of the image of the x-rays hitting a luminescent panel. Lunar PIXImus software (version 1.45) was used to calculate the ratio of attenuation of the high and low energies to separate bone from soft tissue compartments and, within the soft tissue compartment, to separate lean tissue mass from fat mass and thus determine the bone mineral density (BMD), total bone mineral content (BMC), fat composition (% fat), and total tissue mass (TTM) in the regions of interest (total body for all tests, and additionally, vertebrae and both femurs for BMD). Previous studies have determined that this technique precisely measures fat and lean tissue mass, and that there is a close relationship between fat and lean tissue mass estimated by this technique with those measured using chemical carcass analysis (Nagy and Clair, 2000, Obesity Research 8:392-398).

Body composition and percent body fat was measured in eight (8) heterozygous and four (4) wild-type mice; half were males and half were females. There was no difference between groups in any of the parameters measured (TTM, % fat, total body BMD, femur BMD, vertebrae BMD and total body BMC).

Mouse body weight was determined to the nearest 0.1 gm using an Ohaus Scout scale. Body length was determined from nose to the base of tail and is reported in cm. Body weight and body length data were obtained for mice at eight (8) weeks of age. The body weight of thirty (30) heterozygous (+/−) mice (ten (10) males and twenty (20) females) and thirteen (13) wild type (+/+) mice (seven (7) males and six (6) females) was determined and analyzed. There was no significant difference in body weight between groups.

Body length data was determined and analyzed for eight (8) heterozygous (+/−) mice and four (4) wild type (+/+) mice; half of the animals were male and half were female. There was no significant difference in body length between groups.

6.1.3 the Effect of ENZ66 Disruption on Hematology and Blood Chemistry

Whole blood was collected by retro-orbital bleed and placed in a capillary blood collection tube that contained EDTA. The blood was analyzed using the Cell-Dyn 3500R analyzer (Abbott Diagnostics). The analyzer employs dual technologies to provide the basis for a five-part white blood cell (WBC) differential identification. Multi-Angle Polarized Scatter Separation (MAPSS) provides the primary white blood cell count and differential information, while impedance provides additional information in the presence of fragile lymphocytes and hypotonically resistant red blood cells. Approximately 135 microliters of whole blood is aspirated into the analyzer using a peristaltic pump. Four independent measurement techniques are used by the Cell-Dyn 3500R System to obtain the hematologic parameters. The WBC Optical Count (WOC) and the WBC differential data are measured in the optical flow channel, resulting in the identification of the WBC subpopulations (neutrophils, lymphocytes, monocytes, eosinophils, and basophils) for the five part WBC differential. The WBC Impedance Count (WIC) is measured in one electrical impedance channel. The RBC and platelet data are measured in a second electrical impedance channel. The hemoglobin is measured in the spectrophotometric channel. The sample was aspirated, diluted, mixed, and the measurements for each parameter were obtained during each instrument cycle. The final hematological analysis parameters obtained are white blood cell count, neutrophils, lymphocytes, monocytes, eosinophils, basophils, red blood cells, hemoglobin, hematocrit, platlets, red cell distribution width, mean corpuscular volume, mean corpuscular hemoglobin, mean corpuscular hemoglobin concentration and mean platelet volume.

Blood samples were obtained from a total of twelve (12) mice. Analysis and comparison of the blood samples obtained from four (4) wild-type mice and eight (8) heterozygous ENZ66 mice revealed that disruption of the ENZ66 gene results in no significant difference in the levels of the hematological parameters examined.

Approximately 200 microliters of whole blood was collected from the retro-orbital plexus. The blood was placed in a 2.5 ml micro-collection tube and centrifuged to obtain the serum. The sample was analyzed for the following analytes: albumin, alkaline phosphatase, alanine aminotransferase (ALT), total bilirubin, blood urea nitrogen (BUN), calcium, glucose, phosphorus, cholesterol, triglycerides, creatinine and uric acid using a Cobas Integra 400 (Roche Diagnostics). The Cobas Integra 400 is a random and continuous access, sample selective analyzer. The analyzer uses four measuring principles: absorbance photometry, turbidimetry, fluorescence polarimetry and ion-selective electrode potentiometry to assay the analytes described above.

A total of twelve (12) mice were analyzed: four (4) mice were-wild-type (+/+) with normal ENZ66 expression; and eight (8) mice were heterozygotes (+/−). There were no significant differences in any of the above analytes between the two groups.

The mononuclear cell profile is derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples are analyzed using a Becton Dickinson FACSCalibur flow cytometer with CellQuest software. All leukocytes are identified by CD45 staining, and granulocytes are excluded by scatter. T cells are identified by expression of TCR b-chain, and are further divided into CD4+CD8− (mature helper) and CD4−CD8+ (mature cytotoxic/suppressor). NK cells and B cells are identified from the TCRb- (non-T) population by staining with pan-NK and CD19 antibody, respectively. Monocytes are defined as CD45+ mononuclear cells which are negative for all T, B, and NK markers.

A total of four (4) mice were analyzed: two (2) mice were wild-type (+/+) with normal ENZ66 expression; and two (2) mice were heterozygotes (+/−). There were no significant differences in the percentage of CD4+CD8− or CD4−CD8+ cells, the CD4+/CD8+ ratio, or the percentage of B cells or monocytes between the two groups. However, the percentage of NK cells appears to be slightly reduced in the heterozygous mice (3.9, with a standard error of 0.9) compared to the wild-type mice (7.6, with a standard error of 1.8).

6.1.4 Urinalysis

Approximately 100 microliters of urine was collected by placing the mouse in a clean cage lined with aluminum foil and carefully watching the mouse for urination. Immediately following urination, the sample was collected into a microcollection tube. The specimen was analyzed using a calibrated Chemstrip 101 Urine Analyzer (Ames Diagnostics) urinalysis test strip. The urine was placed on the test pad and was read as indicated by the manufacturer according to the package insert. This urinalysis determines urine osmolality, the presence of leukocytes, nitrite, protein, glucose, ketones, urobilinogen, bilirubin and blood.

Urine samples were obtained from twelve (12) mice. Analysis and comparison of the urine samples obtained from four (4) wild-type mice and eight (8) heterozygous ENZ66 mice revealed no significant differences in the urine analysis parameters examined between the mice of the different genotypes.

6.1.5 Ophthalmology

Slit Lamp Analysis: The slit lamp is a biomicroscope that allows examination of the anatomy of the anterior eye segment, as well as the localization of some abnormalities. It is a rapid and convenient method for preliminary eye examination prior to fundus photography. Mouse eye analysis began with examination utilizing a slit lamp (Nikon, Tokyo, Japan) in combination with a 60 or 90 diopter (D) condensing lens. In preparation for examination, mouse pupils were dilated by adding a drop of 1% cyclopentolate and 1% atropine (Alcon Laboratory Inc., Fort Worth, Tex.) to each eye.

Fundus Photography: Fundus photography is a noninvasive method of examining the eye that is adaptable to high throughput analysis. The appearance of the ocular fundus is representative of overall health. Variation in the appearance of the ocular fundus can be indicative of different diseases, including, but not limited to, diabetes, obesity, cardiovascular disorders, angiogenesis, oxidant related disorders and cancer. Selected animals were subjected to fundus photography using a Kowa Genesis small animal fundus digital camera (Tokyo, Japan) to photograph mouse fundi. The instrument was used with a condensing lens, Volk 60D or 90D (Mentor, Ohio, USA), mounted between the camera and the object to be viewed (mouse eye). In order to avoid complications of anesthesia, such as clouding of the ocular redia, photographs were obtained on conscious mice, whose vibrissae were trimmed with fine scissors to prevent them from obscuring the photograph.

Retinal Angiography: Fluorescein angiography is an established technique used to examine the circulation of the retina. In particular it enables the progression of diabetic retinopathy to be monitored, and provides valuable information on the presence or absence of vascular lesions such as edema (leakage) and ischemia (occlusion of the capillaries). The retinal angiography procedure was similar to the procedure used for fundus photography, except that the standard light was replaced with blue light in combination with a barrier filter. To facilitate imaging, mice were injected intraperitoneally with 25% sodium fluorescein (Akorn Inc., Decator, Ill.) at a dose of 0.01 ml per 5-6 gm body weight. For viewing, the eyepiece was fitted with the manufacturer-supplied barrier filter. The digital imaging system used consists of a camera, a computer, and Komit+software (Kowa, Tokyo, Japan) especially designed for ophthalmological applications, which facilitates image data acquisition, analysis and storage.

The artery to vein ratio (A/V) is the ratio of the artery diameter to the vein diameter (measured before the bifurcation of the vessels). The A/V ratio is measured and calculated according to fundus images. Many diseases will influence the ratio, i.e., diabetes, cardiovascular disorders, papilledema and optic atrophy.

Ophthalmological analysis was performed on twelve (12) mice, four (4) wild-type (+/+) mice and eight (8) heterozygous (+/−) mice, and revealed no significant ophthalmological differences between mice with or without functional ENZ66 alleles.

6.1.6 Neurological and Behavioral Analysis

Functional Observational Battery (FOB): A subset of tests from the Irwin neurological screen (Irwin, 1968, Psychopharmacologia 13:222-257) were used to evaluate the gross neurological function of the mice. This battery of simple neurological tests took 10 minutes and was useful for detecting severe neurological impairments.

Mice were first examined for their overall physical characteristics, such as presence of whiskers, bald patches, piloerection, exopthalmus, palpebral closure, kyphosis, lordosis, and tail abnormalities. The mice were then placed into an empty cage for one minute. Any abnormal spontaneous behaviors such as wild-running, excessive grooming, freezing behavior, hunched body posture when walking, etc., were recorded. Mice were next placed into an empty cage to assess motor reflexes. The cage was quickly moved side to side and up and down. The normal postural reflex is to extend all four legs in order to maintain an upright, balanced position. The righting reflex was measured by turning the mice on their back and determining how long it took the mice to return to an upright position. Normal mice will immediately right themselves. If a mouse did not right itself within 60 seconds, the mouse was returned to its normal upright position.

The eye blink reflex, ear twitch reflex, and flank reflex were measured by lightly touching the eye, tip of the ear, and torso once each with a thin clear piece of plastic. The whisker-orienting response was measured by lightly touching the whiskers with a thin clear piece of plastic while the animal was allowed to move freely. The whiskers are typically moving. When touched the whiskers of normal mice will stop moving and in many cases the mouse will turn its head to the side where the whiskers were touched. To determine a mouse's visual response to light, the mouse was examined in a dimly lit room. Pupil constriction and dilation reflexes were measured by quickly directing a penlight at the mouse's eye and observing pupil constriction and subsequently pupil dilatation once the light source was removed.

The visual reaching response was measured by suspending a mouse by its tail and moving it down towards the edge of a cage. A mouse that can see the cage will reach towards it when the cage is moved in the direction of the mouse.

The tail suspension response was determined by holding the mouse approximately six inches in the air by the tail for 20 seconds and recording normal behaviors such as grabbing of the hindlimbs with the forelimbs and turning up on its sides. If present, abnormal behaviors such as hindlimb and forelimb clutch were also recorded.

The cateleptic response was measured by using a small rod at a fixed vertical position. The mouse was positioned such that its forelimbs were resting on the rod. Normal mice in this situation will quickly remove their forelimbs from the rod. A 60 second time limit was allowed, after which a non-responsive mouse was returned to its normal posture.

The olfactory response was tested by using an odor such as vanilla extract as an olfactory cue. A small amount of vanilla was placed on cotton swab and held behind and to the side of a mouse. If the mouse turns and orients itself to the position of the vanilla extract-containing cotton swab, the result is interpreted as an indication that the mouse can smell this olfactory cue.

Mouse body temperature was determined by gently inserting a small probe into the rectum and recording the temperature with a digital read-out (Physitemp, Clifton). This process took less than 5 sec and the mice appeared calm and unstressed throughout the procedure.

This entire battery of simple neurological tests took about 10 minutes and provided for the detection of severe neurological impairment. At the completion of these tests the mice were returned to their home cage.

Hot Plate Assay for Nociception: Mice were removed from their home cage and placed on a 55.0° C. (+/−0.2° C.) hot plate, and the latency to the first hind limb response was recorded. A Plexiglas enclosure was placed around the subject to keep them from walking off of the plate. The hind paw response is a foot shake, paw lick, or jump. The maximum time allowed for a hind limb response to occur was 30 seconds, after which the mouse was removed if a hind limb response had not occurred.

Open Field Assay for Anxiety Related Responses and Locomotor/Exploratory Activity: Anxiety-related, locomotor, and exploratory responses were measured in a clear Plexiglas (40 cm×40 cm×30 cm) open-field arena. A mouse was placed in the center of the arena and allowed to explore for 20 minutes. Overhead high-level lighting provides additional room lighting to enhance anxiety-related behaviors. Activity in the open field was quantified by a computer-controlled Versamax optical animal activity system (Accuscan Instruments, Columbus, Ohio) containing 16 photoreceptor beams on each side of the arena, thereby dividing the arena into 256 equally-sized squares. An additional set of photobeams was placed above this set to record vertical activity, and a set was placed below to record nose poke activity, thus giving three levels of recordable activity. Total distance traveled (locomotor activity), number of rearing and nose poke events (exploratory activity), and center distance (i.e., the distance traveled in the center of the arena) were recorded. The center distance was divided by the total distance traveled to obtain a center distance:total distance ratio. The center distance:total distance ratio can be used as an index of anxiety-related responses. Data was collected in four-minute intervals over the 20 minute test session.

Rotarod Assay for Motor Coordination: Motor coordination and balance were tested using an accelerating rotarod (Accuscan Instruments, Columbus, Ohio). The test was performed by placing a mouse on a rotating drum (measuring 3 cm in diameter) and recording the time each animal was able to stay on the rotating rod. Some mice hold on to the rotating rod as they begin to fall and ride completely around the rod. The speed of the rod accelerates from 0 to 40 rpm over the length of the 5 minute test. Mice were given four consecutive trials with a maximum time of 300 seconds (5 min).

Prepulse Inhibition of the Acoustic Startle Response: Prepulse inhibition of the acoustic startle response was measured using the SR-Lab System (San Diego Instruments, San Diego, Calif.). A test session began by placing a mouse in the Plexiglas cylinder where it was left undisturbed for 3 min. A test session consists of three trial types. One trial type was a 40 ms, 120 decibel (dB) sound burst alone that is termed the startle stimulus. There were four different acoustic prepulse plus startle stimulus trial types. The prepulse sound is presented 100 ms before the startle stimulus. The 20 ms prepulse sounds are at 74, 78, 82, and 90 dB. Finally, there were trials where no stimulus is presented to measure baseline movement in the cylinders. Six blocks of the six trial types were presented in pseudorandom order, such that each trial type was presented once within a block of seven trials. The average intertrial interval was 15 sec with a range of 10 to 20 seconds. The startle response is recorded for 65 ms (measuring the response every 1 ms) starting at the onset of the startle stimulus. The background noise level in each chamber is approximately 70 dB. The maximum startle amplitude recorded during the 65 ms sampling window (Vmax) was used.

The formula used to calculate % prepulse inhibition of a startle response is:

$$100 - [(\text{startle on acoustic prepulse+startle stimulus trials/startle response alone trials}) \times 100].$$

Four (4) wild type (+/+) mice and eight (8) heterozygous (+/−) mice were analyzed. There were no notable differences in any of the parameters measured between the groups.

6.1.7 Radiology

Heterozygous (+/−) and wild-type (+/+) mice were examined radiologically. In addition, one (1) wild type (+/+) and three (3) heterozygous (+/−) mice were subject to examination using a mouse-size computer aided tomography (CT)

scanning unit, the MicroCAT™ (ImTek, Inc., Knoxville, Tenn.). The mice were injected with a CT contrast agent, Omnipaque 300 (Nycomed Amersham, 300 mg of iodine per ml, 0.25 ml per animal, or 2.50-3.75 g iodine/kg body weight), intraperitoneally. After resting in the cage for approximately 10 minutes, the mice were sedated by intraperitoneal injection of Avertin (1.25% 2,2,2,-tribromoethanol, 20 ml/kg body weight). The CT-scan was done with the anesthetized animal lying prone on the test bed. Three dimensional images were reconstructed by the Feldkamp algorithm in a cluster of workstations using ImTek 3D RECON software.

There were no radiologic findings of significance that differentiated the mice of any genotypic group. The following observations were made for all groups of mice. There were no abnormalities observed in the skull, spine, tail or individual bones. The head, brain and neck appeared normal. The cervical lymph nodes were not enlarged. The lung fields were clear. The hearts were of normal size. The mediastinum and vessels revealed no abnormalities. The liver, spleen and kidneys were normal in size, shape and position. The rate of excretion of contrast media from the kidneys was within normal limits, indicating normal kidney function. The lymph nodes, and other abdominal organs, such as the adrenals, ovaries and prostate were normal. No lesions were observed in the soft tissues (skin, muscle or fat). Additionally, the CAT scans revealed no significant differences between the groups.

6.1.8 Blood Pressure Determination

In an additional study, blood pressure was determined in twenty-four (24) wild-type (+/+) and eleven (11) heterozygous 4 (+/−) mice. Mice were subjected to a conscious systolic blood pressure protocol similar to that previously described (Krege et al., 1995, Hypertension 25:1111-1115). Briefly, mice were placed on a heated platform (37° C.) with their tails placed through a cuff and in a sensor to detect the systolic blood pressure. The blood pressure was measured 20 times a day for 4 consecutive days—the first ten measurements are discarded to allow the animals to acclimate, and then the next ten measurements are recorded.

There was a significant difference in the average systolic blood pressure between the wild-type mice (111.5 mm Hg) and the heterozygous mice (99.8 mm Hg). These data were significant as determined by the Mann-Whitney U-test (p=0.0104).

Additionally, wild-type mice were studied for the effect on blood pressure after injection of an acetylcholinesterase (ACE) inhibitor (enalaprilat), which is known to reduce blood pressure, as a comparison to the reduction in blood pressure seen in the heterozygous ENZ66 mice. Briefly, the baseline blood pressure was measured in twelve (12) mice, and then four (4) mice were injected with 1.25 mg/kg of enalaprilat (high dose), four (4) mice were injected with 0.3125 mg/kg of enalaprilat (low dose), and four (4) mice were injected with saline (control), and the blood pressure was measured at 30 minutes, 2 hours and 6 hours. In the high dose group, the average baseline blood pressure was 104.7 mm Hg, after 30 minutes the average blood pressure was 64.4 mm Hg, after two hours the average blood pressure was 81.7 mm Hg, and after six hours the average blood pressure was 102.2 mm Hg. In the low dose group, the average baseline blood pressure was 113.6 mm Hg, after 30 minutes the average blood pressure was 94.0 mm Hg, after two hours the average blood pressure was 105.6 mm Hg, and after six hours the average blood pressure was 101.9 mm Hg. In the control group, the average baseline blood pressure was 114.1 mm Hg, after 30 minutes the average blood pressure was 113.8 mm Hg, after two hours the average blood pressure was 113.5 mm Hg, and after six hours the average blood pressure was 104.7 mm Hg. Thus, the reduction in blood pressure seen in the ENZ66 heterozygote is comparable to the blood pressure reduction seen upon administration of a known blood pressure-lowering agent, enalaprilat.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07374932B2). An electronic copy of the "Sequence Listing" will also be available from the USPTO upon request and payment of the fee set forth in 37 CFR 1.19(b)(3).

What is claimed is:

1. An isolated nucleic acid molecule comprising a nucleotide sequence encoding the amino acid sequence shown in SEQ ID NO:2.

2. An isolated nucleic acid molecule comprising the nucleotide sequence of SEQ ID NO:1.

3. A recombinant expression vector comprising the isolated nucleic acid molecule of claim 1.

4. The recombinant expression vector of claim 3, wherein said nucleic acid molecule comprises the nucleotide sequence of SEQ ID NO:1.

5. A host cell comprising the recombinant expression vector of claim 3.

* * * * *